United States Patent [19]
Das et al.

[11] Patent Number: 5,989,904
[45] Date of Patent: Nov. 23, 1999

[54] SELECTIVE INHIBITION OF INTERNALLY INITIATED RNA TRANSLATION

[75] Inventors: Saumitra Das; Asim Dasgupta, both of Los Angeles; Peter Coward, San Francisco, all of Calif.

[73] Assignee: The Regents of the University of California, Los Angeles, Calif.

[21] Appl. No.: 08/817,953

[22] PCT Filed: Oct. 11, 1995

[86] PCT No.: PCT/US95/12615

§ 371 Date: Oct. 6, 1997

§ 102(e) Date: Oct. 6, 1997

[87] PCT Pub. No.: WO96/11211

PCT Pub. Date: Apr. 18, 1996

Related U.S. Application Data

[63] Continuation-in-part of application No. 08/321,427, Oct. 11, 1994.

[51] Int. Cl.$^6$ .......................... C07H 21/02; C07H 21/04; C12N 15/85
[52] U.S. Cl. .......................... 435/320.1; 435/6; 435/325; 435/375; 435/455; 536/24.1; 536/24.5
[58] Field of Search ........................... 435/6, 177.3, 375, 435/377, 325, 455; 536/24.1, 24.5; 514/44

[56] References Cited

PUBLICATIONS

Agrawal, S. "Antisense Oligonucleotides: Towards Clinical Trials" TIBTECH vol. 14:376–387, 1996.
Stull et al "Antigene, Ribozyme and Aptamer Nucleic Acid Drugs: Progress and Prospects" Pharmaceutical Research vol. 12(4):465–483, 1995.
Kitamura, N. et al. Primary Structure, Gene Organization and Polypeptide Expression of Poliovirus RNA, *Nature* (1981) 291:547–553.
Racaniello, V.R., et al. Molecular Cloning of Poliovirus cDNA and Determination of the Complete Nucleotide Sequence of the Viral Genome, *Proc Natl Acad Sci* USA (1981) 78:4887–4891.
Skinner, M.A. et al. New Model for the Secondary Structure of the 5' Non–coding RNA of Poliovirus is Supported by Biochemical and Genetic Data Tha Also Show That RNA Secondary Structure is Important in Neurovirulence, *J Mol Biol* (1989) 207:379–392.
Agol, V., The 5'–Untranslated Region of Picornaviral Genomes, *Adv Virus Res* (1991) 40:103–180.
Pelletier, J. et al. Mutational Analysis of Upstream AUG Codons of Polivirus RNA, *J. Virol* (1988a) 62:4486–4492.
Kozak, M., Comparison of Initiation of Protein Synthesis in Procaryotes, Eucaryotes, and Organelles, *Microbiol Rev* (1983) 47:1–45.
Pelletier, J. et al. Internal Initiation of Translation of Eukaryotic mRNA Directed by a Sequence Derived from Poliovirus RNA, *Nature* (1988) 334:320–325.

Jang, S.K. et al. Cap–independent Translation of Encephalomyocarditis Virus RNA: Structural Elements of the Internal Ribonsomal Entry Site and Involvement of a Cellular 57–kD RNA–binding Protein, *Genes Dev* (1990) 4:1560–1572.
Belsham, G.J. et al. A Region of the 5' Noncoding Region of Foot–and–Mouth Disease Virus RNA Directs Efficient Internal Initiation of Protein Synthesis Within Cells: Involvement with the Role of L Protease in Translational Control, *J Virol* (1990) 64:5389–5395.
Jackson, R. et al. The Novel Mechanism of Initiation of Picornavirus RNA Translation, *Trends Biochem Sci* (1990) 15:477–483.
Luz, N. et al. A Cellular 57 kDa Protein Binds to Two Regions of the Internal Translation Initiation Site of Foot–and–Mouth Disease Virus, *FEBS Letters* (1990) 269:311–314.
Luz, N. et al. Interaction of a Cellular 57–Kilodalton Protein with the Internal Translation Initiation Site of Foot–and–Mouth Disease Virus *Virology* (1991) 65:6486–6494.
Bandopadhyay, P.K. et al. Cap–Independent Translation by the 5' Untranslated Region of Theiler's Murine Encephalomyelitis Virus, *J Virol* (1992) 66:6249–6256.
Borman, A. et al. Initiation of Translation of Human Rhinovirus RNA: Mapping the Internal Ribosome Entry Site, *Virology* (1992) 188:685–696.
Borman, A. et al. The Involvement of a Spliceosome Component in Internal Initiation of Human Rhinovirus RNA Translation, *Gen Virol* (1993) 74:1775–1788.
Kohara, K.T. et al. Internal Ribosome Entry Site within Hepatitis C Virus RNA, *J Virol* (1992) 66:1476–1483.

(List continued on next page.)

*Primary Examiner*—John LeGuyader
*Assistant Examiner*—Sean McGarry
*Attorney, Agent, or Firm*—Morrison & Foerster, LLP

[57] ABSTRACT

A method to inhibit translation of an mRNA, which is intitiated at an internal ribosome entry site of the mRNA and requires binding of a protein factor to that site, is disclosed. The method comprises a step of providing, in an in vitro, or in vivo system that is capable of translating the mNRA, an inhibitory effective amount of a molecule that selectively binds to the protein factor, thereby preventing that factor from binding to the mNRA. The inhibitor molecule is an RNA oligonucleotide consisting of less than 35 nucleotides or a structural mimic of such an RNA oligonucleotide. Nucleotide sequences of such inhibitor RNA oligonucleotides include portions of the following sequences: the 60 nucleotide sequence of a yeast inhibitor RNA or of the sequence complementary to that yeast inhibitor RNA; nucleotides 186–220 of poliovirus (stem-loop D); nucleotides 578–618 of poliovirus (stem-loop G); nucleotides 260–415 of poliovirus (stem-loop E); nucleotides 448–556 of poliovirus (stemp-loop F); and the sequence of the internal ribosome entry site of the immunoglobulin heavy chain binding protein (Bip).

4 Claims, 17 Drawing Sheets

PUBLICATIONS

Glass, M.J. et al. Identification of the Hepatitis A Virus Internal Ribosome Entry Site: In Vivo and In Vitro Analysis of Bicistronic RNAs Containing the HAV 5' Noncoding Region, *Virology* (1993) 193:842–852.

Macejak, D.G. et al. Internal Initiation of Translation Mediated by the 5' Leader of a Cellular mRNA, *Nature* (1991) 353:90–94.

Oh, S.K. et al. Homeotic Gene Antennapaedia mRNA Contains 5'-Noncoding Sequences that Confer Translational Initiation by Internal Ribonsome Binding, *Genes Dev* (1992) 6:1643–1653.

Pilipenko, E.V. et al. Prokaryotic–like Cis Elements in the Cap–Independent Internal Initiation of Translation on Picornavirus RNA, *Cell* (1992) 68:119–131.

Brown, B.A. et al. Translation of Poliovirus RNA In Vitro: Changes in Cleavage Pattern and Initiation Sites by Ribonsomal Salt Wash, *Virology* (1979) 97:376–405.

Dorner, H.A. et al. In Vitro Translation of Poliovirus RNA: Utilization of Internal Initiation Sites in Reticulocyte Lysate, *J. Virol* (1984) 50:507–514.

Najita, L., Oxidation—Reduction Sensitive Interaction of a Cellular 50–kDa Protein with an RNA Hairpin in the 5' Noncoding Region of the Poliovirus Genome, *Proc Natl Acad Sci USA* (1990) 87:5846–5850.

Meerovitch, K. et al., A Cellular Protein that Binds to the 5'–Noncoding Region of Poliovirus RNA: Implications for Internal Translation Initiation, *Genes Dev* (1989) 3:1026–1034.

Meervitch, K. et al. La Autoantigen Enhances and Corrects Abberant Translation of Poliovirus RNA in Reticulocyte Lysate, *J. Virol* (1993) 67:3798–3807.

Borovjagin, A.V. et al. RNA—Protein Interactions Within the Internal Translation Initiation region of Encephalomyocarditis Virus RNA, *Nucleic Acids Res* (1991) 19:4999–5005.

Pestova, T.V. et al. Translation of Poliovirus RNA: Role of an Essential cis–Acting Oligopyrimidine Element within the 5' Nontranslated Region and Involvement of a Cellular 57–Kilodalton Protein, *J Virol* (1991) 65:6194–6204.

Chang, K.H. et al. Cell Type–Specific Proteins Which Interact with the 5' Nontranslated Region of Hepatitis A Virus RNA, *J Virol* (1993) 67:6716–6725.

Hellen, C.U.T. et al. A Cytoplasmic 57–kDa Protein that is Required for Translation of Picornavirus RNA by Internal Ribosomal Entry is identical to the Nuclear Pyrimidine Tract–Binding Protein, *Proc natl Acad Sci USA* (1993) 90:7642–7646.

Gebhard, J.R. et al. Specific Interactions of HeLa Cell Proteins with Proposed Translation Domains of the Poliovirus 5' Noncoding Region, *J Virol* (1992) 66:3101–3109.

del Angel, P.A.G. et al. Cell Proteins Bind to Multiple Sites Within the 5' Untranslated Region of Poliovirus RNA, *Proc Natl Acad Sci USA* (1989) 86:8299–8303.

Coward, P. et al., Yeast Cells are Incapable of Translating RNAs Containing the Poliovirus 5' Untranslated Region: Evidence for a Translational Inhibitor, *J Virol* (1992) 66:286–295.

5' ACGGACGCGC GGGUUUCGAA GUAGCAGAAC

AGCGCAGGAA CCCGGGGAAU GGAAGCCCGG 3'    (SEQ ID NO: 2)

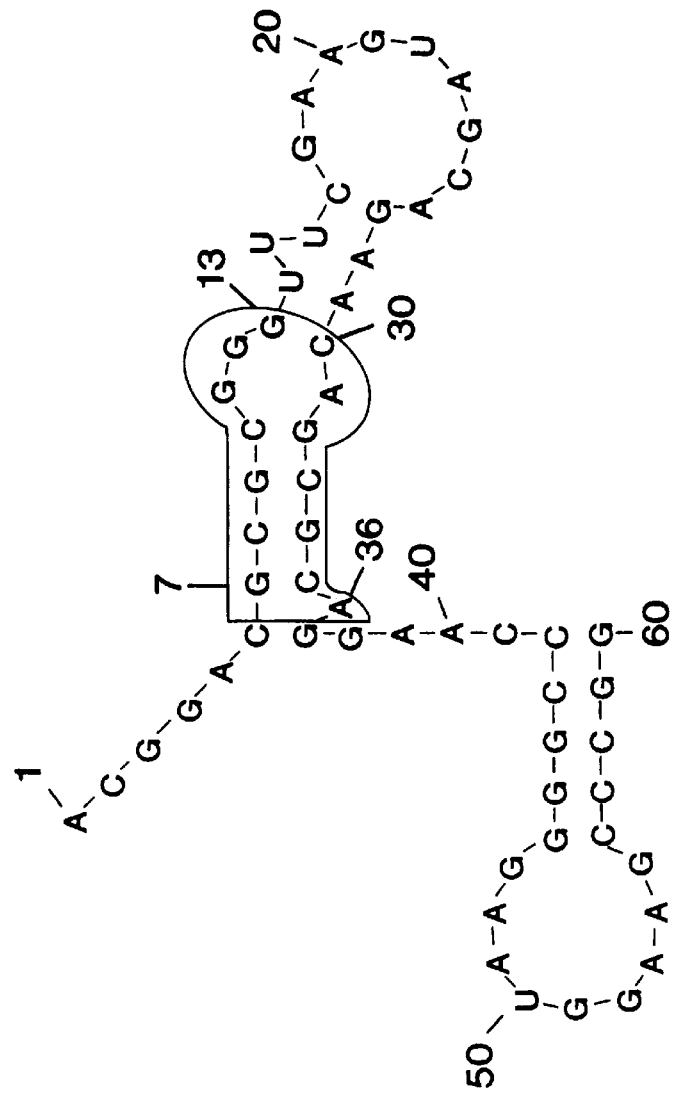
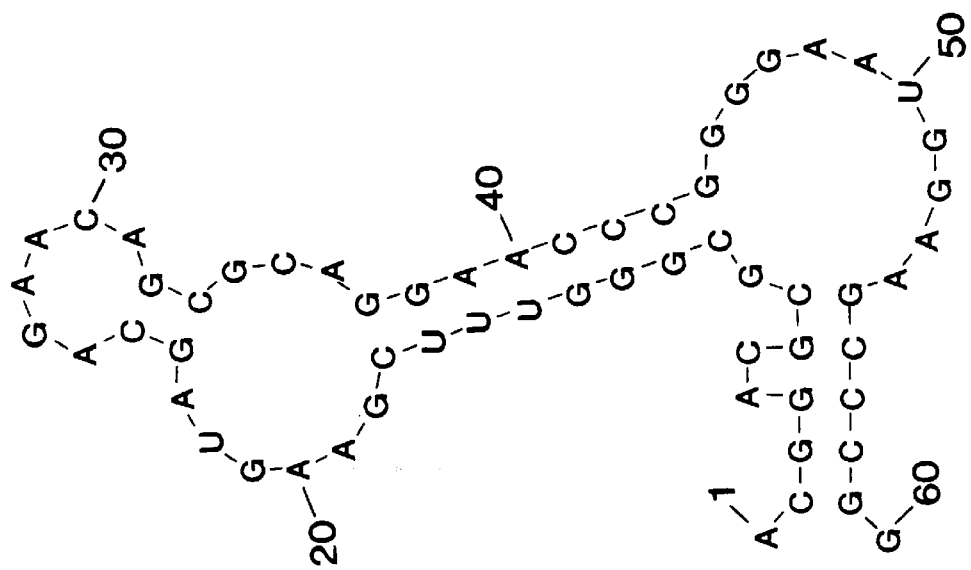
FIG. 15B
FIG. 15A

SEQUENCE LISTING

```
<160> NUMBER OF SEQ ID NOS: 2

<210> SEQ ID NO 1
<211> LENGTH: 14
<212> TYPE: DNA
<213> ORGANISM: Saccharomyces cerevisiae

<400> SEQUENCE: 1
gcgcgggcag cgca                                                      14

<210> SEQ ID NO 2
<211> LENGTH: 60
<212> TYPE: RNA
<213> ORGANISM: Saccharomyces cerevisiae

<400> SEQUENCE: 2
acggacgcgc ggguuucgaa guagcagaac agcgcaggaa cccggggaau ggaagcccgg   60
```

SELECTIVE INHIBITION OF INTERNALLY INITIATED RNA TRANSLATION

This application is a 371 of PCT/US95/12615, and a continuation-in-part of application U.S. Ser. No. 08/321,427 filed 11 Oct. 1994, the disclosure of which is incorporated by reference in its entirety. This invention was made with funding from National Institutes of Health Grant Nos. AI-18272, AI-27451 and AI-38056. The U.S. Government has certain rights in this invention.

TECHNICAL FIELD

The invention relates to selective inhibition of translation of certain mRNAs. More particularly, the invention relates to selective inhibition of an mRNA which is initiated at an internal ribosome entry site, such as a picornavirus RNA, by a small RNA or a molecular mimic thereof. This RNA or mimic interacts specifically with a cellular protein to prevent binding of that protein to the internal ribosome entry site, thereby inhibiting translation initiation at that entry site.

BACKGROUND ART

Picornaviruses include inter alia polioviruses, which cause infantile paralysis, and rhinoviruses, which cause the common cold. Picorna-related viruses, which replicate by mechanisms similar to picornaviruses, include hepatitis A and C, major causes of human hepatitis. Although poliovirus vaccines are available, cases of polio still develop where vaccination is not properly used. Vaccines for other picornaviruses may not be feasible, for instance, due to the high rate of mutability of the viral coat proteins in the rhinoviruses. Therefore, there is a need for methods and compositions for selectively inhibiting picornavirus replication without toxic effects on the host cells.

Poliovirus, the prototype member of the picornaviridae family, is a single stranded, plus-sense RNA virus which multiplies in the cytoplasm of infected cells. The RNA genome comprises approximately 7,500 nucleotides and codes for a 250 kDa polyprotein (Kitamura, N. et al. *Nature* (1981) 291:547–553 and Racaniello, V. R., et al. *Proc Natl Acad Sci* USA (1981) 78:4887–4891. The unusually long 5' untranslated region (5'UTR) of poliovirus RNA (750 nucleotides) is highly structured (Skinner, M. A. et al. *J Mol Biol* (1989) 207:379–392; Agol, V. *Adv Virus Res* (1991) 40:103–180) and contains six to eight upstream AUGs, none of which appears to be used in initiation of translation (Pelletier, J. et al. *J Virol* (1988a) 62:4486–4492.

Translation of most mammalian cellular mRNAs proceeds by binding of ribosomes to the 5' cap structure followed by scanning of the mRNA until the appropriate AUG is encountered by the ribosome (Kozak, M. *Microbiol Rev* (1983) 47:1–45). In contrast translation of naturally uncapped poliovirus RNA has been shown to be mediated by a mechanism involving internal entry of ribosomes near the initiator AUG (Pelletier, J. et al. *Nature* (1988) 334:320–325). Recent studies have demonstrated that internal entry of ribosomes requires an element located between nucleotides 320–631 within the 5'UTR of poliovirus RNA (Pelletier, J. et al., supra). This sequence element has been termed a ribosome landing pad (RLP) or, more generally, internal ribosome entry site (IRES). Although a number of cellular polypeptides have been implicated in IRES-dependent translation, the precise mechanism of internal initiation of translation remains poorly understood.

In addition to poliovirus many other picornaviruses have been shown to utilize this novel mechanism for initiation of translation (Jang, S. K. et al. *Genes Dev* (1990) 4:1560–1572, Belsham, G. J. et al. *J Virol* (1990) 64:5389–5395, Jackson, R. et al. *Trends Biochem Sci* (1990) 15:477–483, Luz, N. et al. *FEBS Letters* (1990) 269:311–314, Luz, N. et al. *Virology* (1991) 65:6486–6494, Bandopadhyay, P. K. et al. *J Virol* (1992) 66:6249–6256, Borman, A. et al. *Virology* (1992) 188:685–696, Borman, A. et al. *Gen Virol* (1993) 74:1775–1788). The RNA genomes of two picorna-related viruses, hepatitis A and C, have been shown to utilize internal ribosome entry for translation initiation (Kohara, K. T. et al. *J Virol* (1992) 66:1476–1483 and Glass, M. J. et al. *Virology* (1993) 193:842–852). Two cellular mRNAs, encoding immunoglobulin heavy chain binding protein (Bip), the mouse androgen receptor (32) and the antennapedia of Drosophila, also have been shown to use internal initiation of translation (Macejak, D. G. et al. *Nature* (1991) 353:90–94 and Oh, S. K. et al. *Genes Dev* (1992) 6:1643–1653).

All picornaviral mRNAs that utilize IRES-dependent translation contain a polypyrimidine tract located at the 3'-border of the IRES sequences within the 5'UTR. Recent evidence indicates that proper spacing between the polypyrimidine tract and the cryptic AUG at nucleotide 586 of the poliovirus 5'UTR is important for viral translation (Jackson et al. (1990, supra), Jang et al. (1990, supra), Pilipenko, E. V. et al. *Cell* (1992) 68:119–131).

Accurate translation of poliovirus mRNA in rabbit reticulocyte lysate requires HeLa cell proteins, indicating involvement of cellular proteins in internal initiation of translation (Brown, B. A. et al. *Virology* (1979) 97:376–405; Dorner, H. A. et al. *J Virol* (1984) 50:507–514). A 50 kDa protein has been shown to interact with the RNA stem-loop structure located between nucleotides 186–221 in poliovirus type 1 RNA (Najita, L. *Proc Natl Acad Sci* USA (1990) 87:5846–5850). The physiological significance of this binding is yet unclear.

Another protein called p52, more abundant in HeLa cells than in rabbit reticulocytes, has been found to specifically bind to the stem-loop structure between nucleotides 559–624 of type 2 poliovirus RNA (Meerovitch, K. et al. *Genes Dev* (1989) 3:1026–1034). This p52 protein appears to be identical to the human La auto antigen (Meerovitch, K. et al. *J Virol* (1993) 67:3798–3807). This nuclear protein, which is recognized by antibodies from patients with the autoimmune disorder lupus erythematosus, leaches out of the nucleus into the cytoplasm in poliovirus-infected HeLa cells. Cell extracts immunodepleted with La antibodies fail to promote cap-independent translation and exogenous addition of purified La protein corrects aberrant translation of poliovirus RNA in reticulocyte lysate which contains little or no p52 (Meerovitch et al. (1993, supra).

UV crosslinking studies have demonstrated another cellular protein, p57 to interact with IRES elements of encephalomyocarditis (EMC), foot-and-mouth disease, rhino-, polio- and hepatitis A viruses (Jang et al. 1990, supra; Borovjagin, A. V. et al. *Nucleic Acids Res* (1991) 19:4999–5005; Luz et al. 1991, supra; Pestova, T. V. et al. *J Virol* (1991) 65:6194–6204; Borman et al. 1993, supra, and Chang, K. H. et al. *J Virol* (1993) 67:6716–6725). It has been demonstrated recently that p57 binding to an IRES of EMCV is identical to that of a polypyrimidine tract binding protein (PTB), which presumably plays a role in a nuclear splicing (Hellen, C. U. T. et al. *Proc natl Acad Sci USA* (1993) 90:7642–7646). Anti-PTB antibody inhibits translation of EMCV and poliovirus RNA and, therefore, PTB may be directly involved in IRES-directed translation.

In addition two other cellular proteins with molecular weights of 38 and 48 kDa have been shown to specifically interact with RNA structures spanning nucleotides 286–456 of poliovirus. These two proteins are reported to be present in HeLa cells in higher quantities than in reticulocyte lysate and appear to be involved specifically in poliovirus translation (Gebhard, J. R. et al. *J Virol* (1992) 66:3101–3109). Another 54 kDa protein cross-links to a region between nucleotides 456–626 and is required for translation of all mRNAs (Gebhard et al. 1992, supra). A recent report indicates the role of a 97 kDa protein in IRES-dependent translation of human rhinovirus RNA (Borman et al. 1993, supra). RNA-protein complex formation has also been demonstrated with the regions encompassing nucleotides 98–182 and 510–629 of the poliovirus RNA (del Angel, P. A. G. et al. *Proc Natl Acad Sci USA* (1989) 86:8299–8303).

Taken together, the results above are compatible with a mechanism of picornaviral translation that involves direct interaction between cellular factors and RNA sequences and/or secondary structures leading to internal initiation. The action of the binding proteins in this mechanism is not known, but transacting proteins may direct ribosomes to enter the mRNA or may alter RNA structure to facilitate ribosome binding.

In a previous study the present inventors have shown that yeast cells are incapable of translating poliovirus RNA both in vivo and in vitro and that this lack of translation represents selective translation inhibition which requires the 5'UTR of the viral RNA (Coward, P. et al. *J Virol* (1992) 66:286–295). The inhibitory effect was found to be due to a transacting factor present in yeast lysate that can also inhibit the ability of HeLa cell extracts to translate poliovirus RNA. Initial characterization of this inhibitor showed that its activity was heat stable, resistant to proteinase K digestion, phenol extraction and DNase digestion, but sensitive to RNase (Coward et al. 1992, supra).

DISCLOSURE OF THE INVENTION

The present invention is directed to methods and compositions for inhibiting translation of an mRNA, such as poliovirus RNA, which is initiated at an internal ribosome entry site and requires binding of a protein factor to that site. The invention is based on the identification of an RNA of 60 nucleotides from the yeast *S. cerevisiae* which inhibits internally initiated translation but not cap-dependent translation. The yeast inhibitor RNA (I-RNA) binds to various cellular proteins that are reported to be involved in internal initiation of translation, competing with the 5'UTR of poliovirus RNA for binding to such proteins, and selectively inhibiting translation of viral mNRA without affecting host cell protein synthesis. When expressed in host cells, the inhibitor RNA specifically and efficiently inhibits translation of poliovirus RNA and thereby protects these cells from viral infection. Analyses of structural requirements of this RNA for inhibition of translation has enabled the design of substantially smaller RNA inhibitors of internally-initiated RNA translation and, ultimately, design of non-RNA molecular mimics of such inhibitor RNAs.

Thus, in one aspect, the invention is directed to a method to inhibit translation of an mRNA, which translation is initiated at an internal ribosome entry site of the mRNA and requires binding of a protein factor to that site. This method comprises a step of providing, in a system that is capable of translating this mRNA, an inhibitory effective amount of a molecule that selectively binds to the required protein factor, thereby preventing that factor from binding to the internal ribosome entry site of the mRNA. In preferred embodiments the inhibitor molecule is an RNA oligonucleotide consisting of less than 35 nucleotides or a structural mimic of such an RNA oligonucleotide.

In other aspects the invention is directed to an expression construct encoding an RNA molecule comprising an RNA oligonucleotide consisting of less than 35 nucleotides linked to a heterologous nucleotide sequence, and to an inhibitor molecule suitable for use in the method of translation inhibition of the invention, which provides the three-dimensional array of intermolecular forces exhibited by an internal ribosome entry site of an mRNA.

More particularly, the invention relates to a method to inhibit translation of an mRNA, which translation is initiated at an internal ribosome entry site of the mRNA and requires binding of a protein factor to said site, which method comprises: a step of providing, in a system that is capable of translating the subject mNRA, a translation inhibitory effective amount of a molecule that selectively binds to the factor, thereby preventing the factor from binding to the site of the mRNA, wherein the molecule is selected from the group consisting of: an RNA oligonucleotide consisting of less than 35 nucleotides; and a structural mimic of said RNA oligonucleotide.

In a preferred embodiment of the method, the mNRA is a viral RNA of a virus selected from the group consisting of picornaviruses, flaviviruses, coronaviruses, hepatitis B viruses, rhabdoviruses, adenoviruses, and parainfluenza viruses. In particular, the virus may be selected from the group consisting of polioviruses, rhinoviruses, hepatitis A viruses, coxsackie viruses, encephalomyocarditis viruses, foot-and-mouth disease viruses, echo viruses, hepatitis C viruses, infectious bronchitis viruses, duck hepatitis B viruses, human hepatitis B viruses, vesicular stomatitis viruses, and sendai viruses. Alternatively, the mRNA to be inhibited may be a cellular mNRA with an internal ribosome entry sites, such as a cellular mRNA encoding an immunoglobulin heavy chain binding protein (Bip).

In the method of the invention, the inhibitor molecule may be provided by adding the RNA oligonucleotide of the invention to the system that is capable of translating the mRNA. Alternatively, the molecule is provided by adding to the system that is capable of translating the mRNA an RNA molecule comprising the RNA oligonucleotide linked to a heterologous nucleotide sequence. The RNA oligonucleotide also may be provided by an expression construct for in situ production of the RNA oligonucleotide in the system that is capable of translating the subject mRNA.

The system to be inhibited by the invention method, that is capable of translating the subject mRNA, may be a cell-free system or a host cell that is infected or at risk of infection with a virus which produces the subject mRNA. The host cell may be a mammalian cell, either in a cell culture or in a host animal in which translation of the subject mRNA is to be inhibited.

In another aspect the invention relates to a molecule that inhibits translation of an mRNA, which translation is initiated at an internal ribosome entry site of this mRNA and requires binding of a protein factor to that site. This molecule selectively binds to the factor, thereby preventing the factor from binding to the ribosome entry site of the mRNA. The invention molecule is selected from the group consisting of an RNA oligonucleotide consisting of less than 35 nucleotides; and a structural mimic of such an RNA oligonucleotide. In preferred embodiments, this molecule is an RNA oligonucleotide having a sequence which comprises at least one portion selected from the group of sequences consisting of the sequence shown in FIG. 1 A; a sequence complementary to the sequence shown in FIG. 1A; the sequence of nucleotides 186–220 of poliovirus (stem-loop D); the sequence of nucleotides 578–618 of poliovirus (stem-loop G); the sequence of nucleotides 260–415 of poliovirus (stem-loop E); the sequence of nucleotides 448–556 of poliovirus (stem-loop F); and the sequence of an immunoglobulin heavy chain binding protein (Bip) mRNA which binds said protein factor to said internal ribosome entry site of said mNRA. In a more preferred embodiment, the nucleotide sequence of the RNA oligonucleotide is the ribonucleotide sequence 5'GCGCGGGCAGCGCA 3'(SEQ ID:1). In other aspects the invention is related to an RNA molecule comprising an RNA oligonucleotide of claim 10 linked to a heterologous nucleotide sequence and an expression construct encoding an RNA molecule wherein the RNA molecule comprises an RNA oligonucleotide of the invention linked to a heterologous nucleotide sequence.

The invention also provides screening assays for identifying molecules that inhibit translation of an mRNA, which translation is initiated at an internal ribosome entry site of this mRNA and requires binding of a protein factor to that site. This inhibitor molecule selectively binds to the translation initiation factor, thereby preventing the factor from binding to the ribosome entry site of the mRNA. Assays to identify initiation factor binding molecules of the invention include immobilized ligand binding assays, solution binding assays, scintillation proximity assays, di-hybrid screening assays, and the like.

In preferred embodiments of the method and molecules of the invention, the protein factor is a 52 kDa La autoantigen. In addition, three other human cellular polypeptides of apparent molecular masses of 80, 70 and 37 kDa may be used to detect molecules which exhibit the translational inhibitory activity of I-RNA of the invention.

BRIEF DESCRIPTION OF THE DRAWINGS

FIG. 1A: Sequence of the 60-nucleotide purified yeast inhibitor RNA [SEQ ID NO:2] was determined as described in materials and methods. 5'- and 3'-termini of the RNA are indicated. FIG. 1B: schematic Illustration of the pSDIR plasmid expressing I-RNA. The position of HindIII and EcoRI restriction endonuclease sites are shown. T7 and SP6 indicate the location of the respective promoters and the arrows show the direction of transcription. FIG. 1C: The I-RNA (sense transcript) was transcribed in vitro using T7 RNA polymerase from plasmid pSDIR linearized with HindIII restriction enzyme. Four micrograms of the synthesized RNA was then mixed with denaturing gel loading dye (US Biochemicals), heated at 55° C. for 10 min and then analyzed on a 1.2% agarose gel along with the 1 kb ladder DNA (BRL) marker (lane M) under conditions for analysis of DNA samples. The position of the I-RNA band on the gel is indicated. FIG. 1D: In vitro translations of pG3CAT and p2CAT RNAs in HeLa cell-free translation lysates were performed in the absence or presence of the inhibitor RNA. Two µg of pG3CAT or P2 CAT RNAs were added per reaction containing 80 µg of HeLa cell lysates. Approximately 4 µg of partially purified yeast inhibitor RNA and 1 µg of synthetic inhibitor RNA were used in respective reactions indicated in the figure. The location of the CAT gene product is shown with an arrowhead.

FIGS. 2A, 2B and 2C: HeLa cell-free translation lysates were used to translate the RNAs listed above the lanes in each panel. In vitro translations were performed with approximately 2 µg of either capped or uncapped RNA as indicated for each deletion mutant construct, in the absence or presence of 1 µg purified I-RNA. Each reaction contained 80 µg of HeLa cell lysate protein. The position of the CAT protein is indicated at the left of FIG. 2A. FIG. 2D: The diagram shows poliovirus 5'-UTR deletion mutant constructs that were used for the above experiment. Vertically hatched boxes represent SP6 RNA polymerase promoters. Solid black boxes represent the sequences from the poliovirus 5'-UTR, and diagonally hatched boxes indicate CAT gene coding sequences. The number underneath the plasmids represents the nucleotide at the edge of the deletion.

FIG. 4A: The numbers at left refer to the approximate molecular masses of the proteins that interact with I-RNA. For competition studies a 100-fold molar excess of the respective unlabeled competitor RNA was added in each binding reaction. The competitor RNAs used were: I-RNA (lane 3), 5'-UTR (lane 4) and nonspecific (Nsp) RNA (lane 5). FIG. 4B: The numbers at left refer to the molecular mass of the protein markers (BRL) (lane M). The numbers at right refer to the molecular mass of each protein which crosslinks to labeled I-RNA probe. 100-fold molar excess of the unlabeled competitor RNAs such as I-RNA (lane 3), UTR 559–624 RNA (lane 4), and nonspecific (Nsp) RNA (lane 5) were used in the binding reactions.

FIG. 6A: The numbers at left refer to the molecular mass of the protein markers (lane M). Individual $^{32}$p-labeled RNA probes such as I-RNA (lanes 1, 2), 5'UTR RNA (lanes 3, 4), stem-loop G RNA (lanes 5, 6) and stem-loop D RNA (lanes 7, 8) were incubated either with (lanes 2, 4, 6, 8) or without (lanes 1, 3, 5, 7) HeLa S-10 extract in the binding reactions followed by UV crosslinking and gel analysis. The numbers at right of FIG. 6A denote the approximate molecular masses of the crosslinked proteins. FIG. 6B: $^{32}$P-labeled stem-loop SL-G (UTR 559–624) and SL-D (UTR 178–224) RNA in lanes 1 and 2, respectively, were incubated with HeLa S-10 extract, crosslinked and analyzed side by side to compare the mobilities of the crosslinked proteins. The numbers at right refer to the estimated molecular masses of the proteins indicated with the arrowheads.

FIG. 7A: Lane 1, no extract; lane 2, extract with no unlabeled competitor RNA; lane 3, unlabeled 5'UTR competitor; lane 4, unlabeled I-RNA competitor; lane 5, unlabeled stem-loop SL-G (i.e., UTR 559–624); lane 6, unlabeled SL-D (i.e., UTR 178–224); lane 7, unlabeled nonspecific RNA; lane 8, unlabeled SL-B RNA (i.e., UTR 51–78); lane 9, unlabeled SL-C RNA (i.e., UTR 124–162). FIG. 7B: Lane 1, no extract; lane 2, extract with no unlabeled RNA;

lane 3, unlabeled 5'SL-G RNA competitor; lane 4, unlabeled I-RNA competitor; lane 5, unlabeled 5'SL-D RNA competitor; lane 6, unlabeled nonspecific RNA competitor; lane 7, unlabeled SL-B RNA; lane 8, unlabeled SL-C RNA. FIG. 7C: Lane 1, no extract; lane 2, extract with no unlabeled competitor; lane 3, unlabeled SL-D competitor; lane 4, unlabeled I-RNA competitor; lane 5, nonspecific RNA; lane 6, unlabeled SL-G competitor; lane 7, unlabeled SL-B RNA; lane 8, unlabeled SL-C RNA. The arrowheads indicate protein-nucleotidyl complexes with proteins of molecular masses of 52, 54 and 57 kDa respectively, from bottom to top.

FIG 8A: The construct pBIP-LUC containing the 5'UTR of Bip mNRA linked to a reporter gene (luciferase) was translated in vitro in HeLa cell lysates in the absence (lane 1) or presence (lane 2) of the yeast inhibitor. As a control the construct pG3CAT was also translated in the absence (lane 3) or presence (lane 4) of the yeast inhibitor. The products were analyzed on a SDS-14% polyacrylamide gel. The arrowhead at the left indicates the position of the luciferase gene product (LUC) and the arrowhead to the right indicates the product of CAT gene (CAT). FIG. 8B: A bicistronic construct pPB310 containing the CAT gene and luciferase gene flanked by TMEV 5'UTR was translated in vitro in HeLa cell lysates in absence (lane 1) or presence (lane 2) of I-RNA. The product were analyzed on a SDS-14% polyacrylamide gel. The arrowheads at left denote the positions of the CAT gene product (CAT) and luciferase gene product (LUC).

FIGS. 10A and 10B show two probable secondary structures of the RNA. The numbers refer to the positions of the nucleotides from the 5'-end of the RNA. The free energy calculated for each predicted structure is given below the respective structure.

FIG. 11A: Inhibition by I-RNA of IRES-mediated translation from bicistronic constructs in HeLa cell extracts. Synthesis of luciferase (Luc) is initiated internally from virus IRES-elements and that of CAT is initiated in a Cap-dependent manner (5'Cap-CAT-IRES-LUC 3'). Lanes 1, 4, 5 and 7 did not contain I-RNA. Lanes 2, 3, 6 and 8 contained 1 µg of I-RNA. FIG. 11B: Effect of I-RNA on in vitro translation mediated by various monocistronic RNAs of immunoglobulin heavy chain binding protein (Bip, lanes 1, 2), CAT (lanes 3, 4, 9, 10), P2 CAT (containing PV 5'UTR, lanes 7, 8), pGemLUC (lanes 5, 6), pCITE (containing EMCV IRES, lanes 11, 12), and yeast α36 mRNA (lanes 13, 14). Lanes 1, 3, 5, 7, 9, 11, 13 contained no inhibitor. Lanes 2, 4, 6, 8, 10, 12, 14 contained 1 µg I-RNA.

FIGS. 15A–15B illustrate the sequence of an active 14 nucleotide BI-RNA containing I-RNA sequences (SEQ ID NO:1) in the context of the computer-predicted secondary structures of the yeast inhibitor RNA as shown in FIG. 10 (SEQ ID NO:2). The solid line in FIG. 15B encompasses the 14 nucleotides of the BI-RNA which were shown to inhibit translation using internal initiation as described in FIG. 14. In the BI-RNA, nucleotide 13 of the native I-RNA structure is linked directly to nucleotide 30, by conventional phosphodiester linkage.

MODES OF CARRYING OUT THE INVENTION

General Description and Definitions

Figures 1A, 1B:
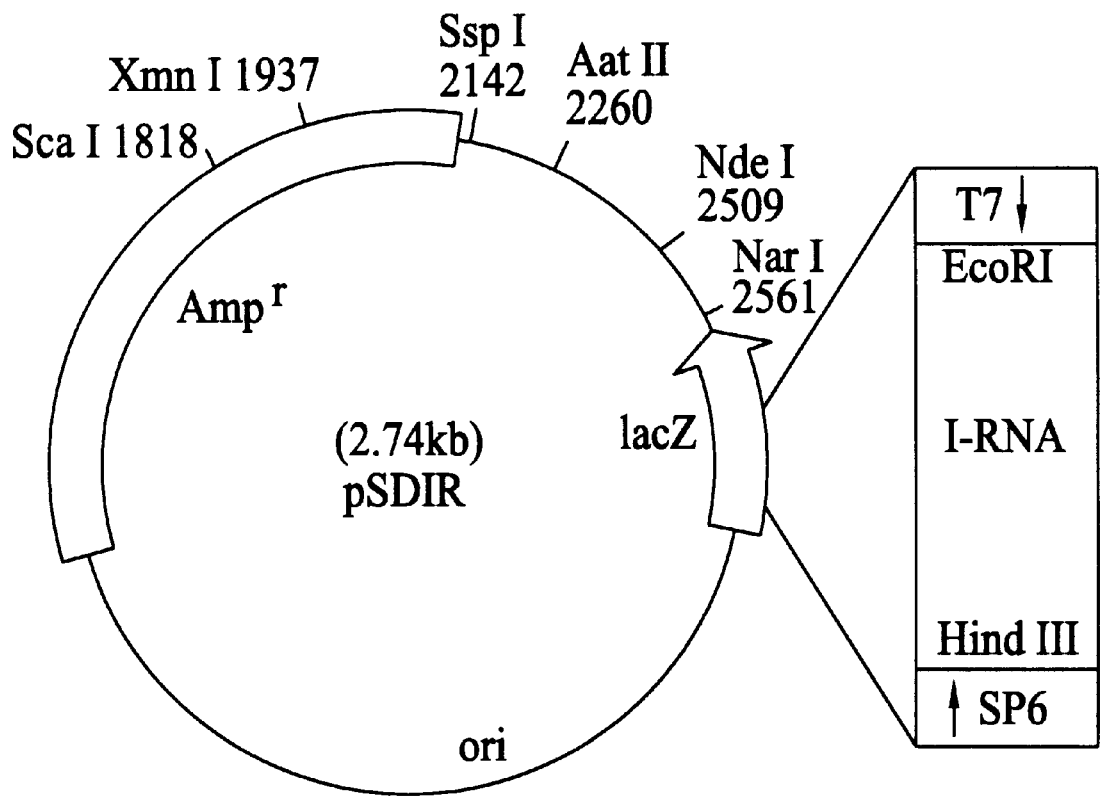
FIG. 1A–1D shows the nucleotide sequence, cloning, expression and activity of the exemplary yeast translation inhibitor RNA (I-RNA).
Figure 1C:
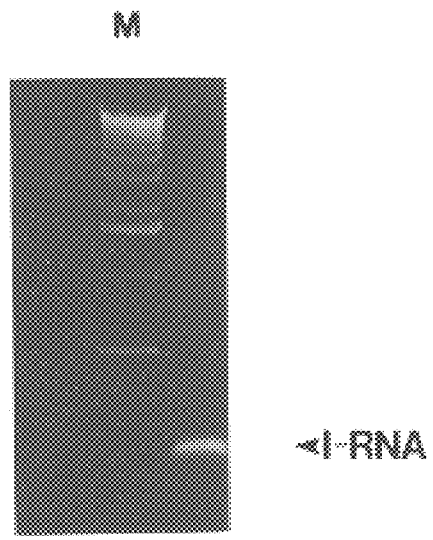

The practice of the present invention will employ, unless otherwise indicated, conventional biochemistry, immunology, molecular biology and recombinant DNA techniques within the skill of the art. Such techniques are explained fully in the literature. See, e.g., Maniatis et al., Molecular Cloning: A Laboratory Manual (1982); DNA Cloning: A Practical Approach, vol. I & II (D. Glover, ed.); Oligonucleotide Synthesis (N. Gait, ed., 1984); Nucleic Acid Hybridization (B. Hames & S. Higgins, eds., 1985); Transcription and Translation (B. Hames & S. Higgins, eds., 1984); Animal Cell Culture (R.

Freshney, ed., 1986); Perbal, A Practical Guide to Molecular Cloning (1984).

The following terminology will be used in accordance with the definitions set out below in describing the present invention.

DNA "control sequences" refers collectively to promoter sequences, ribosome binding sites, polyadenylation signals, transcription termination sequences, upstream regulatory domains, enhancers, and the like, which collectively provide for the transcription and translation of a coding sequence in a host cell.

A coding sequence is "operably linked to" control sequences when expression of the coding sequences is effected when the expression system is contained in an appropriate host cell.

A "host cell" is a cell which has been modified to contain, or is capable of modification to contain, an exogenous DNA or RNA sequence. This includes, for instance, a cell infected by a virus or a cell transformed by a recombinant DNA molecule.

A "heterologous" region of a DNA or RNA construct is an identifiable segment of DNA or RNA within or attached to another nucleic molecule that is not found in association with the other molecule in nature.

Identification of a Translation Inhibitor Molecule

The present invention relates to a method to inhibit translation of an mRNA, which translation is initiated at an internal ribosome entry site of that mRNA and requires binding of a protein factor to said site. The method comprises a step of providing, in a system that is capable of translating the mRNA, a translation inhibitory effective amount of a molecule that selectively binds to the factor, thereby preventing that factor from binding to the ribosome entry site of the mRNA. The translation inhibitor molecule of this invention is selected from the group consisting of an RNA oligonucleotide consisting of less than 35 nucleotides and a structural mimic of said RNA oligonucleotide.

Identification of a translation inhibitor molecule according to the present invention is exemplified in the first instance by the isolation and determination of the 60 nucleotide sequence of a naturally occurring inhibitor RNA from the yeast *S. cerevisiae*. This RNA selectively inhibits internally initiated translation but not cap-dependent translation, for instance, of picornavirus mRNAs. The isolation and sequencing of this small inhibitor RNA (I-RNA) is described in Example 1. Preparation of a synthetic DNA clone encoding the sequence of an inhibitor RNA, and production of the RNA from the synthetic clone by transcription with T7 RNA polymerase, are illustrated in Example 2. These methods may be adapted to the production of other RNA oligonucleotides of the invention, using routine approaches which are well known in the art.

Selective inhibition of translation initiated by internal ribosome entry without substantially affecting cap-dependent translation, according to the invention, may be demonstrated conveniently by in vitro methods using recombinant RNA constructs comprising both IRES- and 5'cap-mediated translation initiation sites. See, for instance, Example 3. Alternatively or in addition, selective inhibition of internally initiated translation may be demonstrated in vitro using recombinant bicistronic mRNA constructs of another viral mRNA, such as those described in Example 7, or of an internally initiated cellular mRNA, such as an mRNA encoding an immunoglobulin heavy chain binding protein as illustrated in Example 8.

The translation inhibitor molecule of the invention selectively inhibits translation from an internal ribosome entry site by binding to a protein factor which is required for initiation of translation at the ribosome entry site, thereby preventing that factor from binding to the ribosome entry site of the mNRA. Such binding of the inhibitor molecule may be using competitive binding methods to show disruption of complexes between the required protein factors and a selected mRNA, such as those described in Example 4 for disruption of complexes between poliovirus RNA sequences and HeLa host cell protein factor by the exemplary yeast I-RNA of the invention. In addition direct binding of an inhibitor molecule of the invention to protein factors required for internal initiation of translation may be demonstrated conveniently using, for instance, the UV-crosslinking method described for the yeast I-RNA molecule in Example 5.

The ability of an inhibitor molecule of the invention to inhibit translation of a viral mRNA in vivo may be demonstrated conveniently in cell cultures as shown for inhibition of poliovirus RNA translation in transfected cells by the yeast I-RNA, which inhibits viral replication and pathogenic effects, as illustrated in Example 9.

Accordingly, based on the general guidance and examples herein, one may determine using routine methods whether a given molecule exhibits the activities of a translation inhibitor of the invention, namely, inhibition of translation of an mNRA, which translation is initiated at an internal ribosome entry site and requires binding of a protein factor to that site, by selectively binding to the factor, thereby preventing the factor from binding to ribosome entry site of the subject mRNA.

Identification of Active RNA Oligonucleotides based on the Yeast I-RNA

In one preferred embodiment the translation inhibitor molecule of the invention is an RNA oligonucleotide, based on the sequence of the exemplary yeast I-RNA, consisting of less than 60 nucleotides, preferably consisting of less than 35 nucleotides, more preferably less than 25 nucleotides, and still more preferably less than 15 nucleotides. As is known in the art it is advantageous to determine the minimum sequence of the I-RNA required for translation inhibition by means of protein factor binding because functional I-RNAs shorter than 60 nucleotides offer greater efficiency in terms of production by conventional chemical synthesis and in terms of their entry into intact cells by diffusion.

To determine which fragment or fragments of the yeast I-RNA exhibits the translation inhibitory activity according to the invention, conventional genetic engineering technology is used to prepare deletion mutants from both 5' and 3'-ends of I-RNA. Ten, 20 or 30 nucleotides are deleted at a time from either the 5' or 3' terminus of the I-RNA. RNA produced from these clones by transcription with T7 RNA polymerase is tested for the ability to inhibit IRES-mediated translation but not cap-dependent translation, as described in the examples herein. Conventional methods are also used to generate a nested set of deletions of 8–10 nucleotide sequences throughout the I-RNA molecule.

These systematic deletional approaches will identify sequences necessary for inhibition of viral translation and binding to host protein factors. Thus, such mutants which inhibit IRES-mediated translation will be tested for loss of binding activity to protein factors such as the p52 factor shown to bind to the yeast I-RNA or other factors mentioned hereinabove (for example p57) which are involved in I-RNA mediated inhibition of viral translation.

Figure 12A:
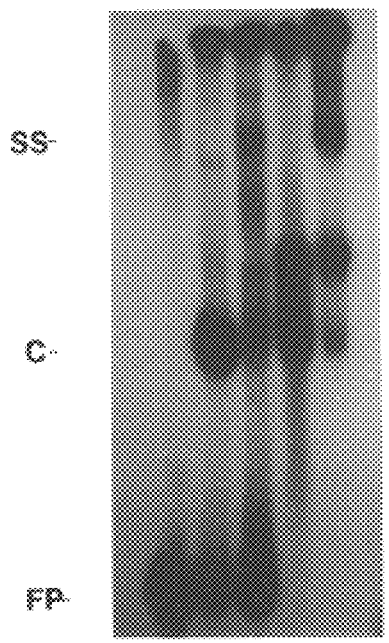
FIGS. 12A–12B show that the HeLa 52 kDa I-RNA-binding protein is identical to La autoantigen. Two assays, gel retardation followed by supershifting with La-antibody FIG. 12A, and UC-crosslinking followed by immunoprecipitation with La-antibody FIG. 12B, were performed to identify the 52 Kda I-RNA binding HeLa cell protein as the La antigen.
Figure 12B:
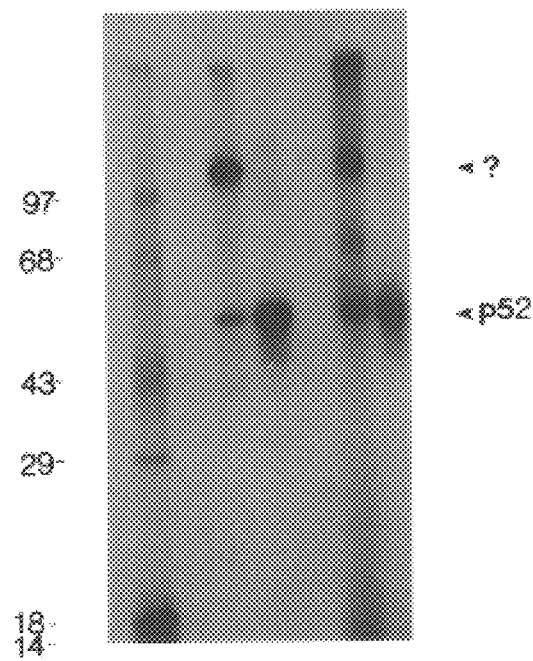

As illustrated in FIG. 12, the p52 factor which binds to yeast I-RNA is identical to the human La autoantigen as shown by immunological assays. This identity was further confirmed by both immunoprecipitation following UV-crosslinking of the recombinant La protein to I-RNA and the ability to supershift the La-I-RNA complex with anti-La antibody (FIG. 12). That binding of La to I-RNA is relevant to translation inhibition is indicated by the fact that purified recombinant La protein is able to restore PV IRES-mediated translation in the presence of the inhibitor RNA. Additional protein factors which bind to full-length or deleted I-RNAs and which can be used to identify other inhibitor molecules of the invention are described below.

Figure 13:
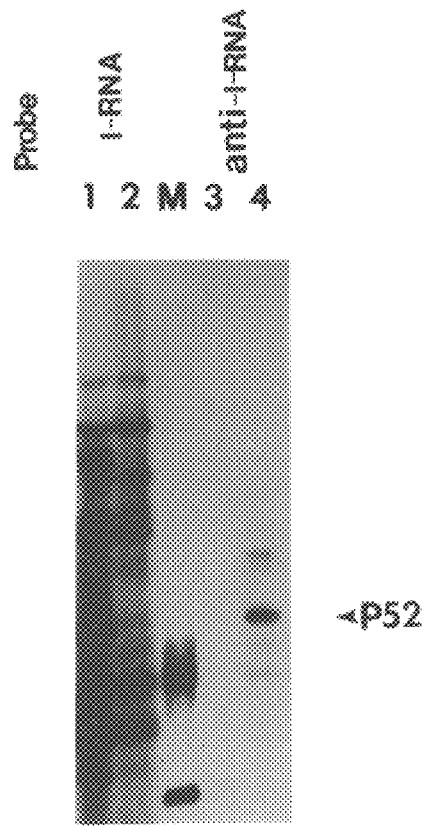
FIG. 13 shows that antisense I-RNA also binds a HeLa 52 kDa protein that interacts with UTR (559–624). UV crosslinking of 32p labeled I-RNA (lane 1 and 2) or antisense I-RNA (lane 3 and 4) with HeLa cell free extract (S10) A 52 kDa protein is complexed to both I-RNA and anti I-RNA (indicated with an arrowhead) which can be competed by cold UTR 559–624 (lane 2). Lane M contained 14C labeled protein molecular mass markers with sizes of 43 and 29 kDa respectively from the top. (A) Gel retardation: $^{32}$P-labeled I-RNA probe was incubated with 50 µg of HeLa S10 extract (lanes 2 and 3 ) or with 0.3 µg of purified La protein expressed from the clone (lanes 4 and 5) in the presence (lanes 3 and 5) or absence (lanes 2 and 4) of antibody of La protein. I-RNA-protein complexes formed (denoted by C) with HeLa S10 or purified La protein were both super shifted (indicated by SS) with anti-La antibody. Preimmune IgG did not alter the migration of the complex (C). (B) $^{32}$P-I-RNA (lanes 1, 2 and 3) or 32p UTR 559–624 RNA (lanes 4, 5 and 6) were UV-crosslinked to HeLa S10 proteins (lanes 2 and 5) or purified La protein (lanes 3 and 6). After RNase digestion protein-nucleotidyl complexes were immunoprecipitated using anti-La antibody. Preimmune IgG did not recognize the 52 kDa (La)-I-RNA complex, but recognized a nonspecific protein migrating at ~110 kDa indicated by a question mark (data not shown).

A more selective mutational analysis also may be used to identify an active oligonucleotide of the invention based on the larger sequence of an active I-RNA such as the exemplary yeast I-RNA. In particular, it has been found that an antisense RNA having the sequence exactly complementary to the sequence of yeast I-RNA is as efficient in binding p52 as the sense I-RNA molecule. See FIG. 13. This result taken together with the fact that there is no apparent sequence homology of the yeast I-RNA with poliovirus RNA sequences bind host cell protein factors needed for initiation of translation suggest that secondary structure of I-RNA may play a crucial role in the inhibition of internal initiation of translation. Thus, many aspects of the secondary structure of a sequence complementary to any RNA would be expected to be similar to the secondary structure of the sequence itself, since generally the same intrastrand base pairings would be able to form in the complementary strand as in the original sequence.

Figure 10B:
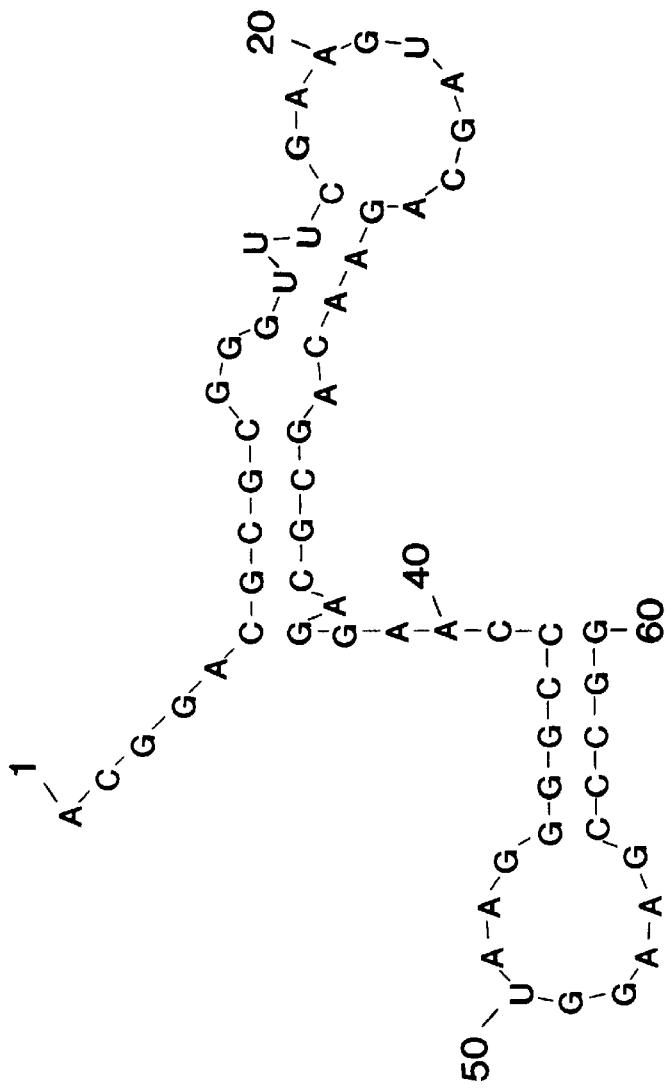
FIGS. 10A–10B illustrate computer-predicted secondary structures of the yeast inhibitor RNA (SEQ ID NO:2).
Figure 10A:
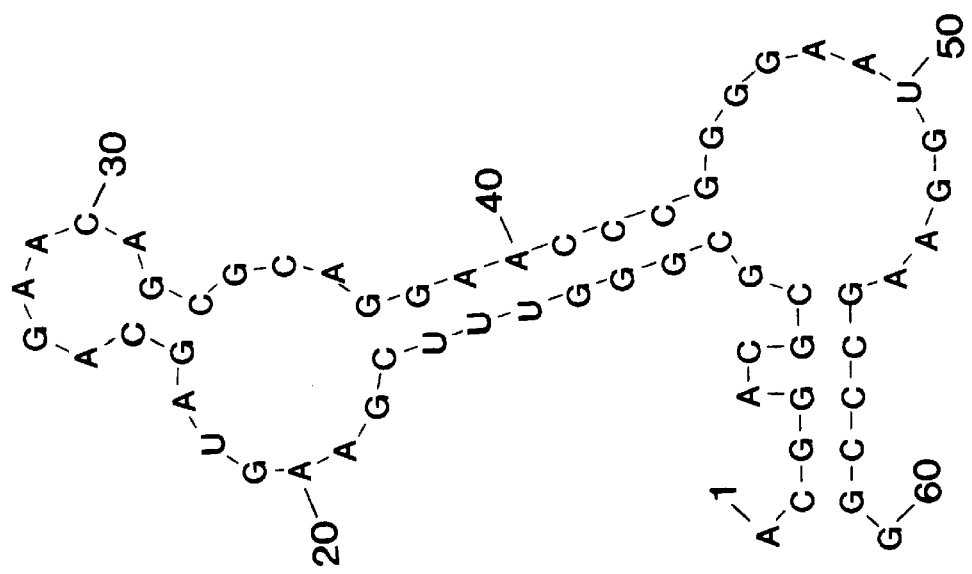

Indeed, two computer-predicted secondary structures of the I-RNA have been generated that are thermodynamically relatively stable having ΔG of −27 and −21 Kcal/mol (FIG. 10). (These structures were predicted using commercially available software called DNASyS, but other similar software is widely known and available. See, for instance Pilipenko et al. (1992, supra), Jackson et al. (1990, supra) and Dildine, S. L. et al. (1992, supra). These secondary structures partly resemble a p52 binding site on the poliovirus mRNA.

Further, the secondary structure of the 60 nucleotide long native I-RNA (FIG. 10) does not change significantly by addition of 11 extra nucleotides generated during the exemplary cloning procedure. Accordingly, by appropriate analysis of secondary structures, one can predict whether linking of an active RNA oligonucleotide of the invention to a heterologous sequence is likely to destabilize the secondary structure of the oligonucleotide and thereby destroy its translation inhibitory activity. In addition the retention of the required activity may be readily determined for any desired RNA oligonucleotide using the routine methods described herein.

Figure 14:
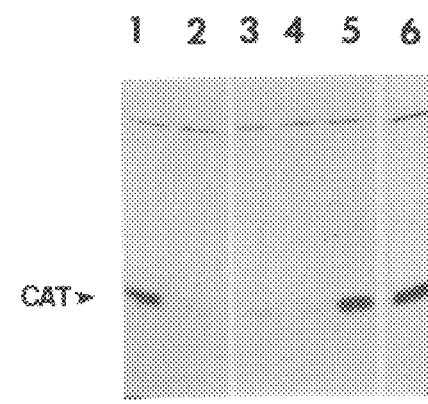
FIG. 14 shows inhibitory activity of a 14 nucleotide long RNA (BI-RNA) containing I-RNA sequences in specifically inhibiting translation by internal initiation (P2 CAT) but not cap dependent translation (CAT). The figure shows translation of CAT gene (indicated with an arrowhead) from P2 CAT (lanes 1–4) or pCAT (lane 5 and 6) construct in the absence (lane 1 and 5) or presence of either I-RNA (lane 2) or 1 µg (lane 3 and 6) and 2 µg (lane 4) of BI-RNA.

By testing RNA oligonucleotides corresponding to various loops in the predicted secondary structures of the yeast I-RNA, a 14 nucleotide long fragment of I-RNA was found to specifically inhibit poliovirus IRES-mediated translation. See FIG. 14. It should be noted that the testing of RNA oligonucleotides comprising loops in computer-predicted secondary enables identification of active RNA oligonucleotides containing noncontiguous portions of the larger I-RNA sequence, such as the exemplary 14 nucleotide fragment which consists of nucleotides 7–13 covalently coupled (by conventional 5'-3' phosphodiester linkage) to nucleotides 30–36 of the yeast I-RNA.

Experimental results of a systematic deletional analysis of the yeast I-RNA are illustrated in Example 10, below. This analysis shows that the minimum I-RNA sequence required to inhibit PV IRES-mediated translation appears to reside between nucleotides 30–45. This conclusion is supported by two observations. First, a deletion mutant (I-3 RNA) which contains the entire I-RNA sequence except nucleotides 31–45 is totally inactive in inhibiting viral IRES-mediated translation. Second, a truncated I-RNA (nt 30–45, I-9 RNA) retains considerable amount of translation-inhibitory activity.

However, a 25 nt long truncated RNA (I-7 RNA) containing the I-9 RNA sequence appears to be more active particularly in vivo. The shorter I-9 RNA was only 50% as active as I-RNA in vivo. Both I-7 and I-9 RNAs can assume secondary structures having stem-and-loop sequences. Clearly, because of smaller size, I-9 RNA is much less stable than I-RNA which may affect stability of I-9 RNA inside a cell. Known thio-derivatives or other nuclease-resistant nucleotide analogs may be used to increase stability and thus activity of I-9 RNA or other inhibitor RNAs of the invention which are exogenously provided to cells. The structure(s) of I-RNA or its truncated derivatives may be important in IRES-mediated translation inhibition. The fact that addition of an extra ten nucleotides to the 3'-end of I-7 RNA (nt 26–50) significantly reduces its (1–6 RNA, nt. 26–60) translation-inhibitory activity may be indicative of alteration of structure of this RNA which should be avoided in designing the 3'-end of an inhibitor RNA of the invention. Similarly addition of another 5 nucleotides to the 5'-end of I-6 RNA drastically reduces its (I-5, nt 20–60) ability to inhibit translation, indicating a need to consider such 5'-end effects in inhibitor RNA design.

Another alternate approach to identify a sequence and secondary structure responsible for translation inhibition, for instance by p52 binding, is to determine if a domain of I-RNA bound to p52 is resistant to RNase digestion according to routine methods known in the art. In this approach $^{32}$P-body labeled I-RNA is incubated with purified pR2 under binding conditions. The resulting complex is digested with micrococcal nuclease or a mixture of RNases T1, T2, and A. The mixture is then analyzed for one or more protected fragments following phenol extraction and ethanol precipitation. Protected fragment of 1-RNA are sequenced directly, for instance, using a commercially available sequencing kit. An alternate sequencing approach is to hybridize the protected fragment with cDNA encoding the I-RNA, followed by digestion of single stranded regions of the hybrid and sequence determination of the protected DNA fragment which is comparatively easier than RNA sequencing. The protected fragment is then tested for specific competition with unlabeled I-RNA but not with a non-specific RNA for translation inhibition and binding to the protein factor, as described herein.

Besides the p52 La autoantigen protein, other protein factors have been identified which bind to I-RNA or deletion mutants thereof and therefor may be used (e.g., in binding assays) to identify other molecules having the translation inhibition activity of the I-RNA of the invention. UV-crosslinking studies utilizing various labeled RNAs and competition experiments demonstrated that both I-7 and I-4 mutant I-RNAs bound two common polypeptides namely 52 and 37 kDa (see Example 11). However, these two RNAs differed from each other in that I-7 RNA bound a 80 kDa polypeptide whereas I-4 RNA interacted with a 70 kDa polypeptide. Therefore, in addition to the 52 and 37 kDa polypeptides, binding of the 80 kDa protein to the viral 5'-UTR may be important for internal initiation to occur and I-7 RNA may directly compete with the 5'-UTR in binding these polypeptides. A recent report by Meyer et al. utilizing UV-crosslinking studies indicates the importance of a 80 kDa protein in IRES-mediated translation of foot-and-mouth disease virus (FMDV) (Meyer, K., A. Petersen, M. Niepmann and E. Beck (1995) J. Virol. 69:2819–2824). This 80 kDa protein has been identified as initiation factor, eIF-4B. The results presented by Meyer et al. suggest that additional protein factors contribute to this interaction of eIF-4B with FMDV IRES. Therefore, binding of eIF-4B to viral IRES may require La and 37 kDa polypeptides and or other polypeptides. I-7 RNA may interfere with IRES-mediated translation by binding these polypeptides. Accordingly, ability to interfere ultimately with binding of the 80 kDa protein is expected to be an indicator of an inhibitor having the translation inhibition activity of the I-RNA of the invention.

Despite their interactions with 52 and 37 kDa polypeptides I-4 and I-8 RNAs may not efficiently inhibit translation because of their inability to interact with the 80 kDa polypeptide. Binding of the 70 kDa protein to I-4 and I-8 RNA may inhibit their ability to interfere with IRES-mediated translation, perhaps by preventing these RNAs from interacting with the 80 kDa polypeptide. Accordingly, lack of binding to the 70 kDa protein also is expected to be an indicator of an inhibitor having the translation inhibition activity of the I-RNA of the invention.

Identification of Other RNA Sequences for Inhibitory RNA Oligonucleotides

It should be apparent from the above that various additional RNA sequences, besides that of the exemplary yeast I-RNA, may be used to derive additional translation inhibitory RNA oligonucleotides according to the invention. For instance, additional active oligonucleotides may be derived from the complement ("antisense") of the sequence of the yeast I-RNA, since this complementary sequence also shows the translation inhibitory activity of the I-RNA sequence itself. See FIG. 13. The same mutational and other analytical approaches described for the I-RNA sequence are applied, with appropriate routine modifications.

In addition it is apparent that naturally occurring RNA sequences having little or no sequence homology with the exemplary yeast I-RNA may be modified as described herein to produce active RNA oligonucleotides of the invention. Thus, as discussed in the Background above, for instance, it is known that certain loops of the 5'UTR of various picornaviral RNAs, for instance, are responsible for binding of those mRNAs to the protein factors require for IRES-mediated translation initiation. Indeed, the present disclosure shows by deletion analyses that the yeast I-RNA requires the mRNA to have internal ribosome entry site (IRES) sequences to inhibit translation of poliovirus RNA in vitro. Oligonucleotides containing these sequences also will have translation inhibitory activity according to this invention.

However, the prior art does not appear to have recognized the possibility of using for translation inhibition according to this invention an RNA oligonucleotides consisting of the binding sequences of such factor-binding loops, and even the production of such RNA oligonucleotides of less than 35 nucleotides, for any purpose, appears to be unheralded.

Similarly, RNA loops shown to bind to other protein factors besides the p52 protein exemplified in this disclosure are also suitable sources of natural sequences for RNA oligonucleotides of the invention. Additionally, searches for sequences that are similar to I-RNA sequence using FASTA (Pearson et al. 1988) on Biovax copy of GCG-formatted Genbank of three databases, namely viral, structural RNA and plants including yeast (version Sept. 1993) has identified partially related sequences. Thus, 89.5% homology was found (with a 19 nt overlap) with a region of the Japanese encephalitis viral genome. Similarly, 70–80% homology was observed with different regions of genomes of herpes simplex, sindbis, Epstein-Barr, dengue and influenza viruses. When compared against the structural RNA database, the most striking homology (79–100%, 11–19 nt overlap) was with the 16S rRNA from a variety of organisms. The I-RNA also has extensive homology (93.8%, 16 nt overlap) with 5S rRNA of trypanosomes. Comparison against the plant database which includes yeast, showed 93.3% homology (15 nt overlap) with yeast genes of histone H4.1 and H3. The only mRNA found to have homology with I-RNA was maize superoxide dismutase 3 isoenzyme (100% homology, 13 nt overlap). Considering the short length of the overlapping sequences, the significance of these findings is unclear at present; however, these sequences a preferred candidates to test for inhibitory activity of the invention as described herein, particularly those which show appropriate predicted secondary structure.

Identification of Structural Mimics of an Active RNA Oligonucleotide

To determine what secondary structure within the l-RNA molecule is important for its translation inhibitory activity, site-directed mutagenesis is performed by changing one or two nucleotides at a time to destabilize I-RNA secondary structures.

Two computer-predicated secondary structures of the I-RNA can be envisioned that are relatively thermodynamically stable. These computer-predicted, secondary structures of I-RNA are confirmed by determining its (their) accessibility to modifications with dimethyl sulfate (DMS) and sensitivity to single- and double-strand specific nucleases. These methods have been used to support computer-predicted secondary structures of PV5'UTR.

Briefly I-RNA is treated with DMS, S1, cobra venom (CV), as well as other nucleases as described (11). For the identification of sites where modifications and cleavages have occurred, primer extension technique will be used (11). Elongation of DNA chains should stop one nucleotide before the modified base and just before the cleaved internucleotide bond. Initial deletion studies described earlier and experimentally verified secondary structure of 1-RNA allow determination which nucleotides to mutate within I-RNA. On finding mutations which destabilize secondary structures of I-RNA which also destroys its biological activity (both in vitro and in vivo), further compensating mutations can be introduced to stabilize the secondary structure which should bring back its biological activity, thereby creating structural mimics of an RNA oligonucleotide of the invention.

In addition structural mimics with enhanced resistance to nucleases or permeability to membranes may be synthesized using convention nucleotide analogs known in the art and testing for activity as described herein.

Further, a general method of obtaining an analog of a molecule that binds to an analyte is described in U.S. Pat. No. 5,133,866. This describes and claims method to identify a paralog useful for the conduct of affinity chromatography with respect to an analyte which has specific affinity for a first moiety in comparison to additional moieties present in the environment of the first moiety which method comprises: screening, for ability to selectively bind said first moiety a panel of individual candidate paralogs, wherein said candidate paralogs have systematically varied values of at least two different parameters, each of which parameters determines the ability of the paralog to bind other substances. The method includes candidate paralogs which are nucleic acids. The method makes possible the systematic and facile selection of a substance capable of specific binding to any selected moiety. If the selected moiety is a receptor or other biological target, the paralog will be useful in a variety of pharmacological and therapeutic applications.

Screening Assays for Inhibitors of the Invention

In vitro assays for identifying molecules which inhibit protein translation by the same mechanism as the yeast I-RNA of the invention, such as antibodies or other compounds that modulate the activity of a protein translation initiation factor which binds to an internal ribosome entry site and which is inhibited by binding to the yeast I-RNA of the invention, also are provided by the invention. Such assays may involve an immobilized ligand, for example, immobilizing a suitable initiation factor required for IRES-dependent protein translation initiation or a molecular mimic of such a factor, or, alternatively, a natural ligand to which such an initiation factor binds (e.g., I-RNA), detectably labelling the nonimmobilized binding partner, incubating the binding partners together and determining the effect of a test compound on the amount of label bound wherein a reduction in the label bound in the presence of the test compound compared to the amount of label bound in the absence of the test compound indicates that the test agent is an inhibitor of initiator factor binding.

Another type of assay for identifying compounds that modulate the interaction between a translation initiation factor and a ligand is a scintillation proximity assay which involves immobilizing the factor or a mimic or fragment thereof on a solid support coated (or impregnated with) a fluorescent agent, labelling the ligand with a compound capable of exciting the fluorescent agent, contacting the immobilized initiation factor with the labeled ligand in the presence and absence of a putative modulator compound, detecting light emission by the fluorescent agent, and identifying modulating compounds as those compounds that affect the emission of light by the fluorescent agent in comparison to the emission of light by the fluorescent agent in the absence of a modulating compound. Alternatively, the initiation factor ligand may be immobilized and initiation factor may be labeled in the assay.

Yet another method contemplated by the invention for identifying compounds that modulate the interaction between an IRES-dependent protein initiation factor and a ligand is a di-hybrid screening assay. This assay involves transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of a IRES-dependent translation initiation factor and either the DNA binding domain or the activating domain of the transcription factor, expressing in the host cells a second hybrid DNA sequence encoding part or all of the ligand and the DNA binding domain or activating domain of the transcription factor which is not incorporated in the first fusion, evaluating the effect of a putative modulating compound on the interaction between initiation factor and the ligand by detecting binding of the ligand to initiation factor in a particular host cell by measuring the production of reporter gene product in the host cell in the presence or absence of the putative modulator, and identifying modulating compounds as those compounds altering production of the reported gene product in comparison to production of the reporter gene product in the absence of the modulating compound. Presently preferred for use in the assay are the lexa promoter, the lexa DNA binding domain, the GAL4 transactivation domain, the lacZ reporter gene, and a yeast host cell. Variations of the di-hybrid assay may include interactions of La or p80 proteins interacting with other components of the translation apparatus.

A modified version of the foregoing assay may be used in isolating a polynucleotide encoding a protein that binds to a translation initiation factor by transforming or transfecting appropriate host cells with a DNA construct comprising a reporter gene under the control of a promoter regulated by a transcription factor having a DNA-binding domain and an activating domain, expressing in the host cells a first hybrid DNA sequence encoding a first fusion of part or all of the initiation factor and either the DNA binding domain or the activating domain of the transcription factor, expressing in the host cells a library of second hybrid DNA sequences encoding second fusions or part or all of putative initiation factor binding proteins or RNAs and the DNA binding domain or activating domain of the transcription factor which is not incorporated in the first fusion, detecting binding of an initiation factor binding protein or RNA to the initiation factor in a particular host cell by detecting the production of reporter gene product in the host cell, and isolating second hybrid DNA sequences encoding initiation factor binding protein or RNA from the particular host cell.

An additional assay for a translation inhibitor having the activity of the I-RNA of the invention is an La-dependent in vitro translation assay. This approach is based on direct observation of inhibition of IRES-mediated in vittro translation as described in the examples. Alternatively, compounds may be screened for inhibition of IRES-dependent translation in transfected cells, for instance, using a bicistronic RNA molecule with one protein product being translated in a CAP-dependent fashion and the second protein product translated via IRES, as described in Example 10, for instance. Such a screen may be based on inhibition of IRES-dependent translation of a reporter molecule from a cell culture. In addition, screening for inhibitors also may utilize detection of inhibition of virus production (either capsid protein as described in Example 10 or via plaque assay. Ultimately, an animal-based screen for compounds that block production of picornavirus-mediated effects in an animal model system is used to evaluate efficacy of I-RNA mimics.

Use of the Inhibitor Molecules and Related Aspects of the Invention

The methods and inhibitor molecules of the invention may be used for the treatment or prevention of viral infections in cells or in animal or human subjects. It also may be used as a diagnostic tool to determine whether a particular RNA show IRES-mediated translation which generally indicates a viral mNRA.

As to the range of viruses suitable for the invention, the inhibitory RNA from yeast specifically inhibits IRES-mediated translation by a variety of picornaviral RNAs including those of poliovirus, rhinovirus, hepatitis A virus, coxsackievirus, and other members of the picornaviridae group. Translation of capped cellular mRNAs does not appear to be affected by this yeast inhibitor RNA in vitro or in vivo, whereas picornaviral replication is inhibited by the yeast inhibitor RNA in vivo due to inhibition of viral RNA translation. The inhibitor RNA specifically binds proteins which interact with RNA structural elements within the viral 5'UTR.

Many other viruses not belonging to the picornaviral group also use internal ribosome entry for translation. A prime example is a flavivirus, hepatitis C (1, 2). The yeast inhibitor also inhibits hepatitis C virus translation. Recently, it has been reported that mRNA 3 of infectious bronchitis virus, a coronavirus, also utilizes internal ribosome entry mechanism (3, 4). In addition, mRNAs encoding reverse transcriptase of duck and human hepatitis B virus, vesicular stomatitis virus NS protein, adenovirus DNA polymerase, and Sendai virus P/C protein have been shown to use internal initiation of ribosome entry (5–9). Further still, internal ribosome entry has been shown for translation in the retrovirus family (e.g., murine leukemia virus; ref. 29), the pestivirus family (30), and plant poty viruses (31). Thus, antiviral agents against members of many different virus groups which utilize internal initiation of translation may be prepared according to the present invention.

The inhibitory RNAs and structural mimics of the invention can also be used to control the translation of an internally initiated mRNA, such as a viral mRNA, in a cell culture or host organism harboring such a mRNA. The inhibitory RNA or mimic is supplied using standard methods of administration, such as those set forth in Remington's Pharmaceutical Sciences, Mack Publishing Company, Easton, Pa., latest edition. Preferably, for in vivo treatment of a subject, the RNA or mimic is provided by injection, and formulated using conventional excipients therefor, such as Ringer's solution, Hank's solution, and the like. Oral administration with proper formulation can also be effected. While most administration is systemic, in the case of localized conditions such as a nasal infection by rhinovirus, administration may be topical or otherwise local. Slow release mechanisms for drug delivery may also be used.

Alternatively, the inhibitory RNA sequence may be generated in situ by providing an expression system which scontains a DNA encoding the RNA or inhibitory effective fragment thereof in a "reverse orientation" expression system. The expression system may either be designed to be operable in the host subject, such as a mammalian subject wherein the reverse oriented sequence is under the control of, for example, an SV-40 promoter, an adenovirus promoter, a vaccinia virus promoter or the like, so that the RNA is transcribed in situ. When used in a culture of host cells, the expression system will be provided on a replicon compatible with the host cells.

More in particular, the yeast I-RNA of the invention has been shown to inhibit IRES-dependent initiation of translation from the 5'UTR of picornaviruses including human picornaviruses (poliovirus, rhinoviruses, hepatitis A and coxsackievirus B3) and an animal picornavirus (foot-and-mouth virus; FMDV), as well as internal translation of a flavivirus (hepatitis C) mRNA. Further, mRNA 3 of infectious bronchitis virus, a coronavirus which causes significant losses in the poultry industry, also utilizes an internal ribosome entry mechanism (3, 4). In addition, mRNAs encoding reverse transcriptase of duck as well as human hepatitis B virus, vesicular stomatitis virus NS protein, adenovirus DNA polymerase, and Sendai virus P/C protein have been shown to use internal initiation of ribosome entry (5–9). Further still, internal ribosome entry has been shown for translation in the retrovirus family (e.g., murine leukemia virus; ref. 29), the pestivirus family (30), and plant poty viruses (31). Accordingly, this invention also enables production of transgenic animals and transgenic plants, using available genetic engineering technology, which express an I-RNA molecule or related translation initiation inhibitor of the invention and thereby are resistant to pathogenic effects of viruses in which the I-RNA inhibits IRES-dependent translation. We contemplate the production of transgenic plants and animals, by conventional techniques, that are resistant to viruses and other pathogens whose replication depends upon internal initiation of translation.

Another aspect of the invention relates to isolation and modification of I-RNA genes in cells, particularly in yeast cells, which express an I-RNA of the invention that prevents IRES-dependent translation initiation of a desired mRNA in such cells or extracts thereof. These genetic modifications inhibit expression or activity of the I-RNA, thereby allowing the desired IRES-dependent translation initiation. In the first instance, identification of the sequence of the I-RNA molecule isolated from yeast, as described herein, enables preparation of a labeled probe which can be used with conventional genetic engineering methods detect the I-RNA gene (e.g., by Southern blotting) and its initial transcription product (e.g., by Nothern blotting). Further, using such a probe, preferably under stringent hybridization conditions, the yeast I-RNA gene or homologous genes from other species or transcripts of such genes may be isolated by standard gene cloning approaches well known in the art. For example, a random genomic library of a desired species may be screened by hybridization using an I-RNA probe provided by the invention. Examination of the structure and genomic organization of the yeast I-RNA gene and homologous genes from other species will provide a better understanding of the normal function of such genes.

In addition, the present disclosure enables modifications of host cells to inhibit expression or activity of I-RNA. In the first instance, introduction of such modifications will determine whether I-RNA activity is essential for survival of host cells which express such I-RNAs. In one approach, an RNA having a sequence complementary to the I-RNA (i.e., an "antisense I-RNA") is expressed in a host cell (e.g., yeast) which expresses an I-RNA molecule. The vector for expression of the antisense I-RNA contains a selectable marker gene (e.g., URA 3) to ensure that only transformed cells are recovered. If no transformed cells expressing antisense I-RNA are recovered, inducible expression constructs may be tested to determine whether the antisense RNA vector can be transformed into the cell in absence of antisense I-RNA expression and whether subsequent expression inhibits any cellular function(s). Alternatively, the I-RNA gene may be eliminated using gene "knock out" methodology known in the art. For instance, in yeast cells exogenous DNA introduced into the cell efficiently and stably integrates into chromosomal DNA by homologous recombination, allowing efficient replacement of a wildtype gene with a non-functional copy. Typically, the non-functional copy is generated by replacing wildtype coding sequences with a selectable marker gene (e.g., LEU or URA). Transformation of diploid cells may circumvent possible lethal effects if some I-RNA activity is required for cell viability. Yeast or other I-RNA-expressing host cells, or extracts thereof, which have reduced I-RNA activity as a result of either an antisense or gene knock out modification according to the invention, are useful for expression of mRNAs requiring IRES-dependent translation initiation. Also contemplated are yeast or other I-RNA host cells which can be modified by gene knockout methodologies, as known in the art, to remove the gene encoding La or homologs thereof to produce host strains that are permissive for expression of proteins whose synthesis is dependent upon internal initiation of translation.

The following examples are intended to illustrate, but not to limit, the invention.

EXAMPLE 1

Purification and Sequencing of the Yeast Inhibitor RNA

The *Saccharomyces cerevisiae* strain used was ABYSI (provided by D. Meyer, UCLA). The inhibitor from yeast cells capable of specifically inhibiting IRES-dependent translation from poliovirus RNA was initially purified by passage through a DEAE-Sephacel column (Coward et al. 1992, supra). The inhibitor bound strongly to the column and was eluted by washing the column with 1M potassium acetate. Further purification of the DEAE-Sephacel purified inhibitor involved DNase and proteinase K digestion followed by phenol-chloroform extraction. Finally, RNA obtained by alcohol precipitation of the aqueous phase was end-labeled with $\gamma^{32}$P-ATP at the 5'-end, and single RNA bands were resolved by 20% PAGE/8M urea electrophoresis. Each RNA band was eluted from gel slices and was assayed for its ability to inhibit internal initiation of translation from a poliovirus 5'UTR-CAT construct but not from a control CAT construct known to initiate translation in a cap-dependent manner (Pelletier et al. 1989). A single band which migrated as an RNA of 60 nucleotides was associated with the inhibitory activity.

More in particular, yeast cell lysates were prepared as described previously (Rothblatt et al. 1986) except that they were not treated with micrococcal nuclease. Lysates were loaded onto a DEAE Sephacel (Pharmacia) column at 0.1M potassium acetate and step-eluted with buffers containing 0.3, 0.6 and 1M potassium acetate. The fractions were dialyzed back to 0.1M salt and assayed for translation inhibitory activity. The 1M fraction which showed inhibitory activity was subjected to DNase treatment followed by proteinase K digestion and phenol-chloroform extraction. The RNA from this fraction was then isolated by alcohol precipitation. The yeast RNAs that copurified with the 1M fraction were then dephosphorylated and 5' end labeled by kinase reaction. Labeled RNA species were separated on a 20% acrylamide-8M urea sequencing gel. Labeled and cold RNA bands were run in parallel lanes and were eluted from the gel as follows. Individual gel slices were soaked in 500 µl of elution buffer (2M ammonium acetate and 1% SDS) at 37° C. for 4 hr. After a brief centrifugation at room temperature the supernatant was collected, extracted with phenol:chloroform (1:1), and alcohol precipitated in the presence of 20 µg of glycogen (Boehringer-Mannheim Biochemicals).

The precipitated RNA pellets were resuspended in nuclease-free water and tested for the ability to inhibit translation of p2CAT RNA (Coward et al. 1992, supra) in the HeLa cell-free translation system. HeLa cells were grown in spinner culture in minimal essential medium (GIBCO laboratories) supplemented with 1 g/L glucose and 6% newborn calf serum. HeLa cell extracts were prepared as previously described (Rose et al. 1992; Coward et al. 1992, supra). In vitro translation in HeLa cell-free extracts was performed essentially as described earlier (Rose et al. 1978). Two micrograms of each mRNA were used with 80 µg of HeLa cell extract in a 25µl reaction mixture in presence of 25 µCi of $^{35}$S-methionine (800 Ci/mmol; Amersham) and 40 units of RNasin (Promega).

Translation in rabbit reticulocyte lysate (Promega) was performed in 15 µl reaction volumes that contained 12.5 µl of the lysates, 2 µg of mNRA with 25 µCi of $^{35}$S-methionine (specific activity>1000 Ci/mmol) at 30° C for 1 hr. Three microliters of the translation product was analyzed by sodium-dodecyl sulfate (SDS) - 14% polyacrylamide gel electrophoresis.

The purified RNA was sequenced using a commercially available sequencing kit (US Biochemicals Corporation). The end-labeled RNA was mixed with base specific ribonuclease-buffer combination (following the USB-protocol), incubated at 50° C and then loaded onto a 20% acrylamide-SM urea sequencing gel. FIG. 1A shows the sequence [SEQ ID NO:1] of the 60 nucleotide RNA.

EXAMPLE 2

Cloning and Transcription of the Yeast Inhibitor RNA

Based on the determined RNA sequence, sense- and antisense-strand specific deoxyoligonucleotides were synthesized, annealed and cloned into the pGEM 3Z expression vector between the HindIII and EcoRI sites in the polylinker region to form the recombinant plasmid pSDIR (FIG. 1B).

The clone pSDIR was linearized with HindIII restriction enzyme, then transcribed with the T7 RNA polymerase to generate the inhibitor RNA (sense transcript). Transcription by T7 RNA polymerase from the linearized plasmid resulted in synthesis of the inhibitor RNA. When analyzed by gel electrophoresis a single band of 71 nucleotides was observed, comprising the yeast inhibitor RNA and an extra ten nucleotides from the EcoRI site from the 5'-polylinker region, and one nucleotide at the 3'-end from the HindIII site.

Figure 1D:
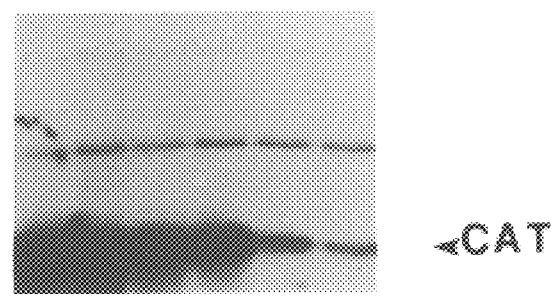

To determine whether the RNA synthesized from the synthetic clone was active, its effect on translation from a CAT construct containing poliovirus 5'UTR at the 5'-end of the CAT gene (P2-CAT) was determined. Both the partially purified inhibitor from yeast and the purified inhibitor transcribed from pSDIR inhibited translation from the P2CAT RNA in vitro in a HeLa cell-free extract (Figure 1D, lanes 4, 5, 6). However, translation from CAT RNA (cap-dependent translation) was not significantly inhibited by either inhibitor (FIG. 1D, lanes 1, 2, 3). Thus, the inhibitor RNA synthesized from the synthetic clone was active in specifically inhibiting poliovirus IRES-dependent translation as previously found with the partially purified inhibitor from yeast cells (Coward et al. 1992, supra).

EXAMPLE 3

Identification of Poliovirus 5'UTR Sequences Required for Inhibition by the Yeast RNA Inhibitor To determine whether specific sequences within the 5'-untranslated region (UTR) of poliovirus RNA are required for the yeast inhibitor RNA to inhibit IRES-dependent translation, a number of deleted 5'UTR-CAT constructs were obtained from the laboratory of Dr. N. Sonenberg (McGill University). See FIG. 2D.

The mRNAs were transcribed in vitro using either T7 or SP6 promoter from different linear plasmids by T7 or SP6 RNA polymerases. Both plasmid pG3CAT and P2CAT (Coward, et al. 1992, supra) were linearized with BamHI and the runoff transcripts were generated using SP6 RNA polymerases. The plasmid pBIP-LUC construct was obtained from P. Sarnow (Macejak et al. 1991) and was linearized with HpaI enzyme and transcribed with T7 RNA polymerase. The TMEV-IRES containing construct pPB310 was from Howard L. Lipton (Bandopadhyay et al. 1992) and was linearized with HpaI and transcribed with T7 RNA polymerase.

Oligodeoxyribonucleotide templates for transcription by T7 RNA polymerase were synthesized on an Applied Biosynthesis DNA synthesizer and then purified. Equimolar amounts of the 18 mer T7 primer oligonucleotide and the template oligonucleotides were mixed in 0.1M NaCl and were annealed by heating at 100° C. for 5 min followed by slow cooling to room temperature. The SL-B, SL-C, SL-D, and SL-G, RNAs were synthesized in vitro following the method described above.

Figure 2A:
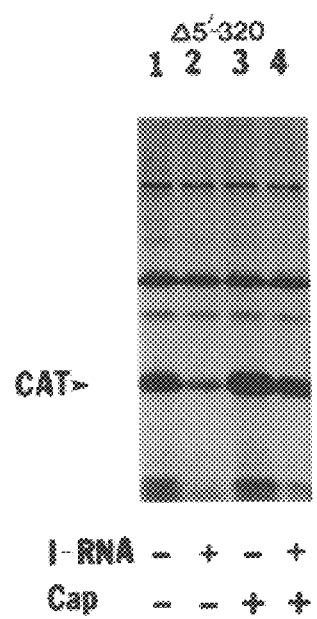
FIGS. 2A–2D illustrate the requirement of the poliovirus 5'UTR sequence for inhibition of translation by the yeast inhibitor RNA.

The inhibitor efficiently inhibited translation from pP2 CAT but not from the pG3 CAT (or pCAT) construct (FIG. 1D). Almost complete inhibition was observed when the Δ5'-33 CAT construct was translated in the presence of the inhibitor RNA (data not shown). Deletion of the first 320 nucleotides from the 5'-end of the UTR did not have a significant effect on the ability of the inhibitor to inhibit translation from the Δ5'-320/CAT construct (FIG. 2A, lanes 1 and 2). Almost 80% inhibition of translation was observed in the presence of the inhibitor (lanes 1 and 2). Some of the inhibition observed with the inhibitor could be reversed when the template RNA was capped prior to translation (FIG. 2A, lanes 3 and 4).

Figure 2B:
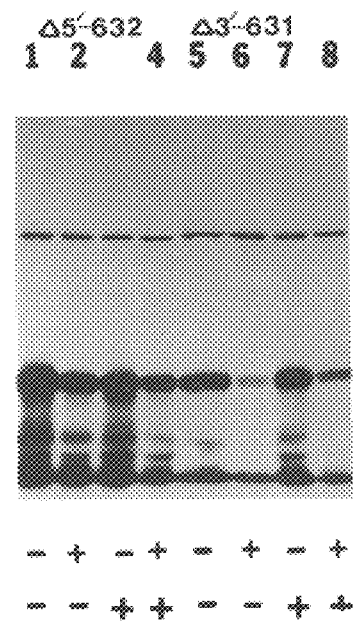

A similar result was obtained with the Δ3'-631/CAT construct; almost complete inhibition of translation from this construct was observed in the presence of the inhibitor and addition of capped RNA reversed inhibition of translation to some extent but not as much as that with Δ5'-320 construct (FIG. 2B, lanes 5–8). In contrast, translation from the Δ5'-632/CAT construct was almost unaffected in the presence of the inhibitor (FIG. 2B, lanes 1 and 2).

Figure 2C:
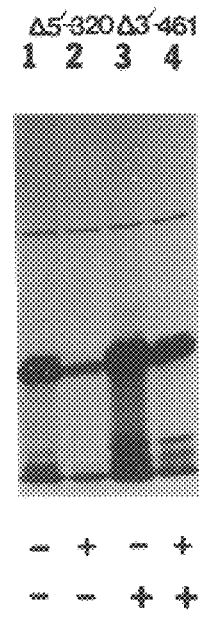
Figure 2D:
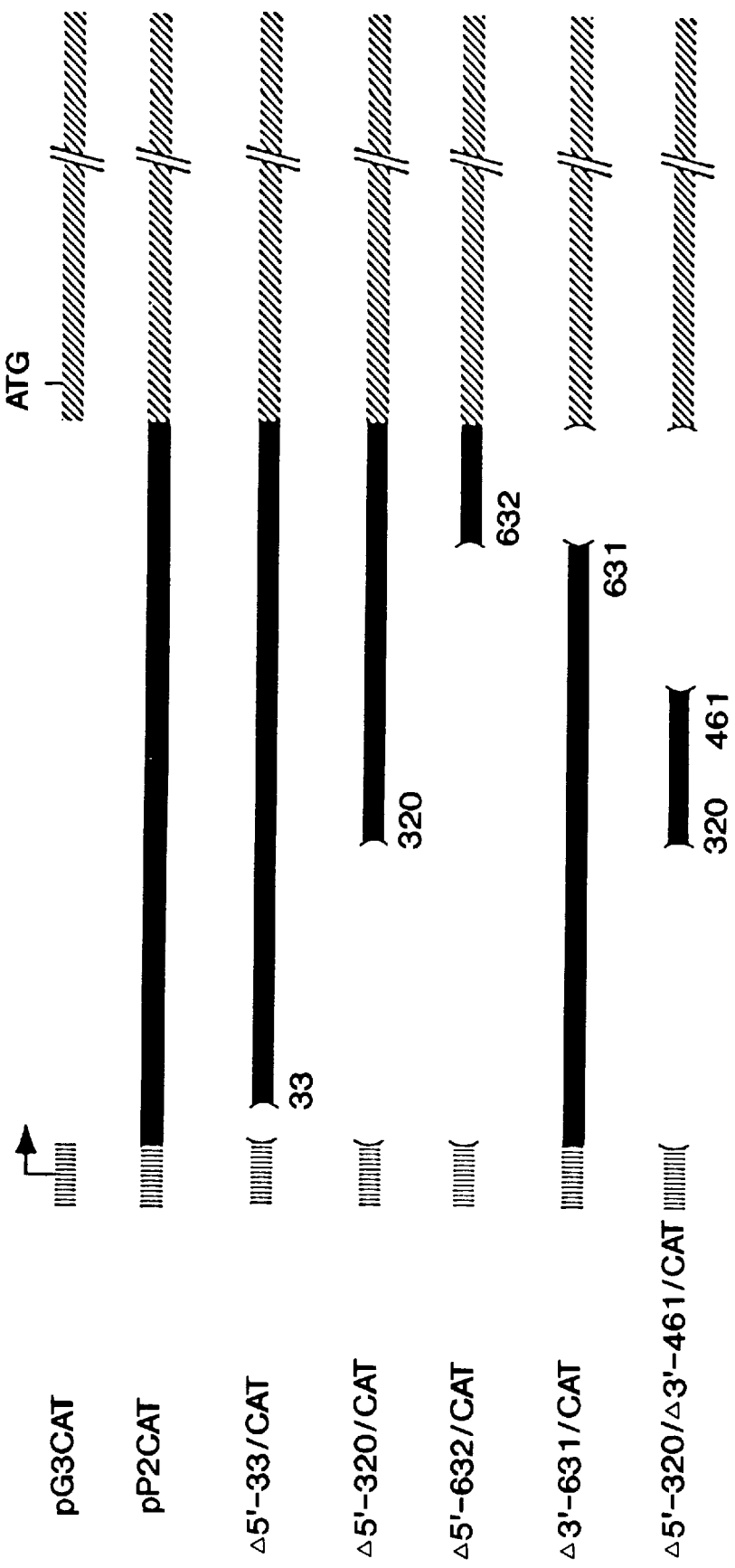

Therefore, almost the entire IRES region of viral RNA (320–631) is required for the inhibitor to efficiently inhibit almost all poliovirus IRES-dependent translation. However, significant inhibition was observed with a construct containing only nucleotides 320–461 of the viral UTR. Thus, translation from the construct Δ5'-320/Δ3'-461/CAT containing only nucleotides 320–461 of the UTR was significantly inhibited by the inhibitor RNA (FIG. 2C, lanes 1 and 2). This inhibition can be overcome to a significant extent by capping the RNA prior to translation (FIG. 2C, lanes 3 and 4), indicating that cap-dependent translation is substantially unaffected by the inhibitor.

EXAMPLE 4

Demonstration of Disruption of Complexes of Protein Factors and mRNA 5'UTR Sequences by Yeast I-RNA using RNA Retardation during Gel Electrophoresis Theoretically, the inhibitor RNA could inhibit IRES-dependent translation by two possible mechanisms: binding to UTR sequences as an antisense RNA or binding to protein factors needed for internal entry of ribosomes. To distinguish these two mechanisms, uniformly $^{32}$P-labeled inhibitor RNA probe was prepared and mixed with HeLa S10 extracts, and the resulting RNA-protein complexes were analyzed by nondenaturing polyacrylamide gel electrophoresis.

HeLa S10 cytoplasmic extract was prepared by collecting the supernatant after centrifugation of the HeLa cell free translation extract at 10,000 g, for 30 min. at 4° C. A 50 μg sample of S10 extract was preincubated at 30° C. for 10 min with 4 μg of poly [d(I-C)] (Pharmacia) in a 15 μl reaction mixture containing 5 mM HEPES pH 7.5, 25 mM KCl, 2 mM $MgCl_2$, 1.0 mM EDTA, 3.8% Glycerol and 2 mM DTT. For competition experiments 10–100-fold excess of the unlabeled competitor RNAs were added to the reaction and incubated for 10 min at 30° C. Finally 5–10 fmole of the labeled RNA probes were added to the respective reaction mixtures and the incubation was continued for another 30 min at 30° C. The nonspecific RNA used in the competition assays was the sequence of the polylinker region (EcoRI to HindIII) of the pGem3Z vector (Promega). Three microliters of the gel loaded dye were added to the reaction mixture to a final concentration of 10% glycerol and 0.2% of both bromophenol blue and xylene cyanol. The RNA-protein complexes were then analyzed on a 4% polyacrylamide gel (39:1-acrylamide:bis) in 0.5X TBE.

As shown in FIG. 3A, a single complex (denoted C) was clearly evident. Increasing concentrations of unlabeled I-RNA competed with the formation of the labeled complex (FIG. 3B, lanes 2–5). A similar result was obtained when unlabeled poliovirus 5'UTR RNA was used for competition. Clearly, at the highest concentration tested UTR sequences successfully competed with I-RNA for binding to HeLa S10 proteins (FIG. 3B, lanes 6–9). An unrelated RNA, however, was not able to compete with labeled I-RNA (FIG. 3B, lane 10). Thus, the inhibitor RNA was able to form a gel-retarded complex with HeLa S10 protein(s) that can be specifically competed with viral 5'UTR sequences.

EXAMPLE 5

Demonstration that the Inhibitor RNA Binds Proteins that Interact with Poliovirus 5'UTR To determine whether specific polypeptides that interact with the viral 5'UTR also interact with the yeast inhibitor RNA, a series of UV-crosslinking experiments were performed. In these experiments the uniformly labeled inhibitor RNA was first incubated with a HeLa S10 extract and then crosslinked using UV light. After ribonuclease treatment, protein-nucleotide complexes were analyzed by SDS-polyacrylamide gel electrophoresis.

Forty to fifty fmole of the $^{32}$P-labeled RNA probes ($8\times10^4$ cpm) were incubated with 50–100 μg of S-10 extract of HeLa cells as described above. After the binding reaction was complete, the samples were irradiated with UV light from a UV lamp (multiband UV-254/366NM Model U GL-25; UVP, Inc.) at a distance of 3–4 cm for 10 min. The unbound RNAs were digested with a mixture of 20 μg of RNase A and 10U of RNase T1 at 37° C. for 30 min and then analyzed on SDS-14% polyacrylamide gels.

Figures 4A, 4B:
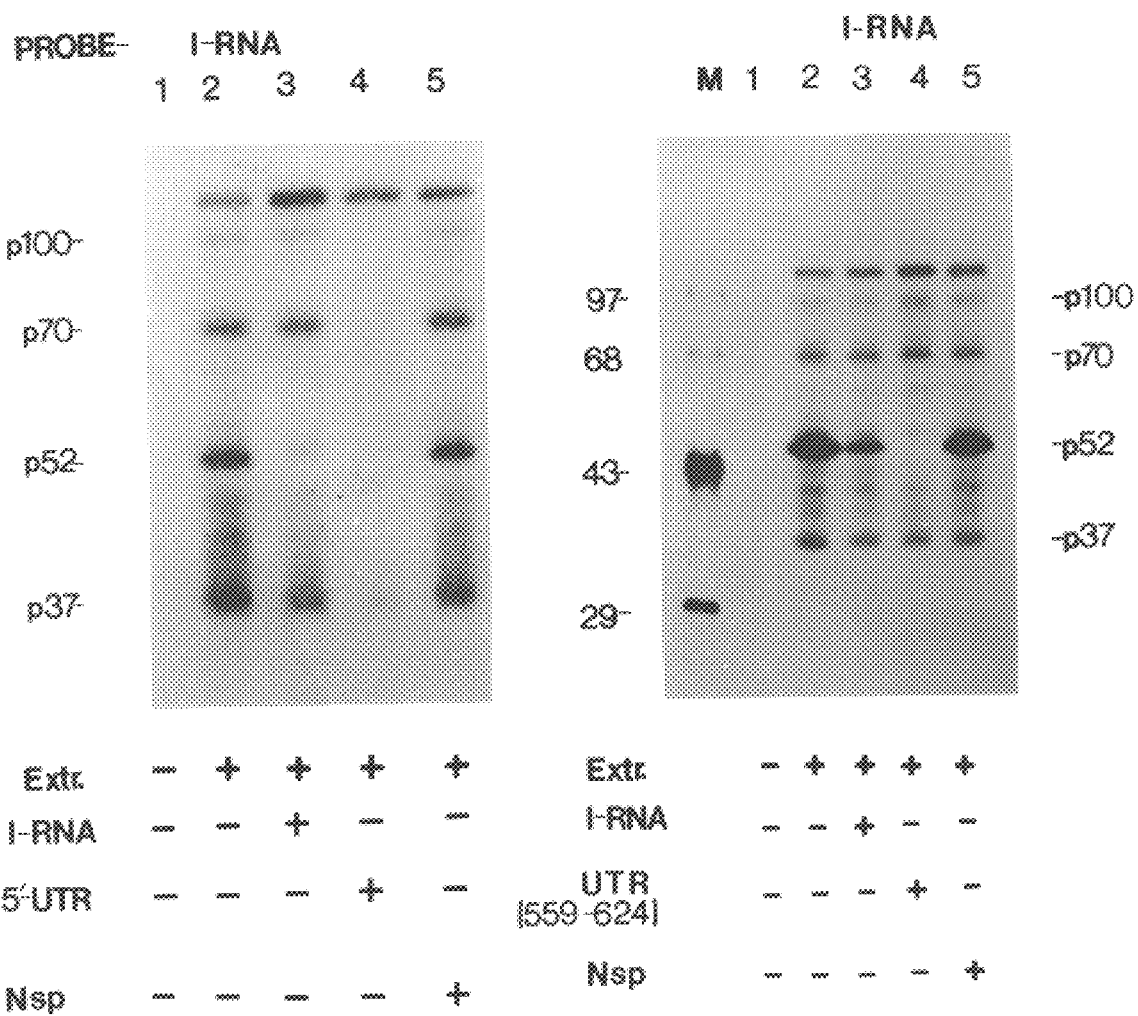
FIGS. 4A–4B show that the I-RNA binds proteins that interact with poliovirus 5'-UTR. UV crosslinking of the $^{32}$p-labeled I-RNA with HeLa cell proteins was performed as described in the examples below.

When $^{32}$P-labeled inhibitor RNA was used to crosslink proteins in HeLa extract, polypeptides having approximate molecular weights of 100, 70, 52, and 37 kDa were detected (FIG. 4A, and 4B lane 2). Among these polypeptides, the 52 kDa protein was most intensely labeled in some experiments (FIG. 4B, lane 2). Addition of unlabeled inhibitor RNA successfully competed with the 52 kDa band (FIG. 4A, lane 3). When unlabeled poliovirus 5'UTR was used as a competitor, the 52 kDa as well as the 100, 70 and 37 kDa bands were completely competed out (FIG. 4A, lane 4). In contrast an unlabeled, unrelated RNA was unable to compete with any of the polypeptides crosslinked to the inhibitor RNA (lane 5).

Because a 52 kDa protein has previously been shown to interact with a specific region of the viral 5'UTR (nucleotides 559–624), the ability of an RNA containing this sequence ("UTR 559–624") to compete with the 52 kDa band crosslinked to labeled I-RNA was determined. As shown in FIG. 4B (lane 4), unlabeled UTR 559–624 completely inhibited formation of the I-RNA-52 kDa complex. Unlike the whole 5'UTR sequence, UTR 559–624 competed with only the 52 kDa protein (compare lane 4 of FIGS. 4A and 4B). These results indicate that the yeast inhibitor RNA binds a 52 kDa protein similar or identical to that bound by poliovirus 5'UTR sequence 559–624.

EXAMPLE 6

Figure 5:
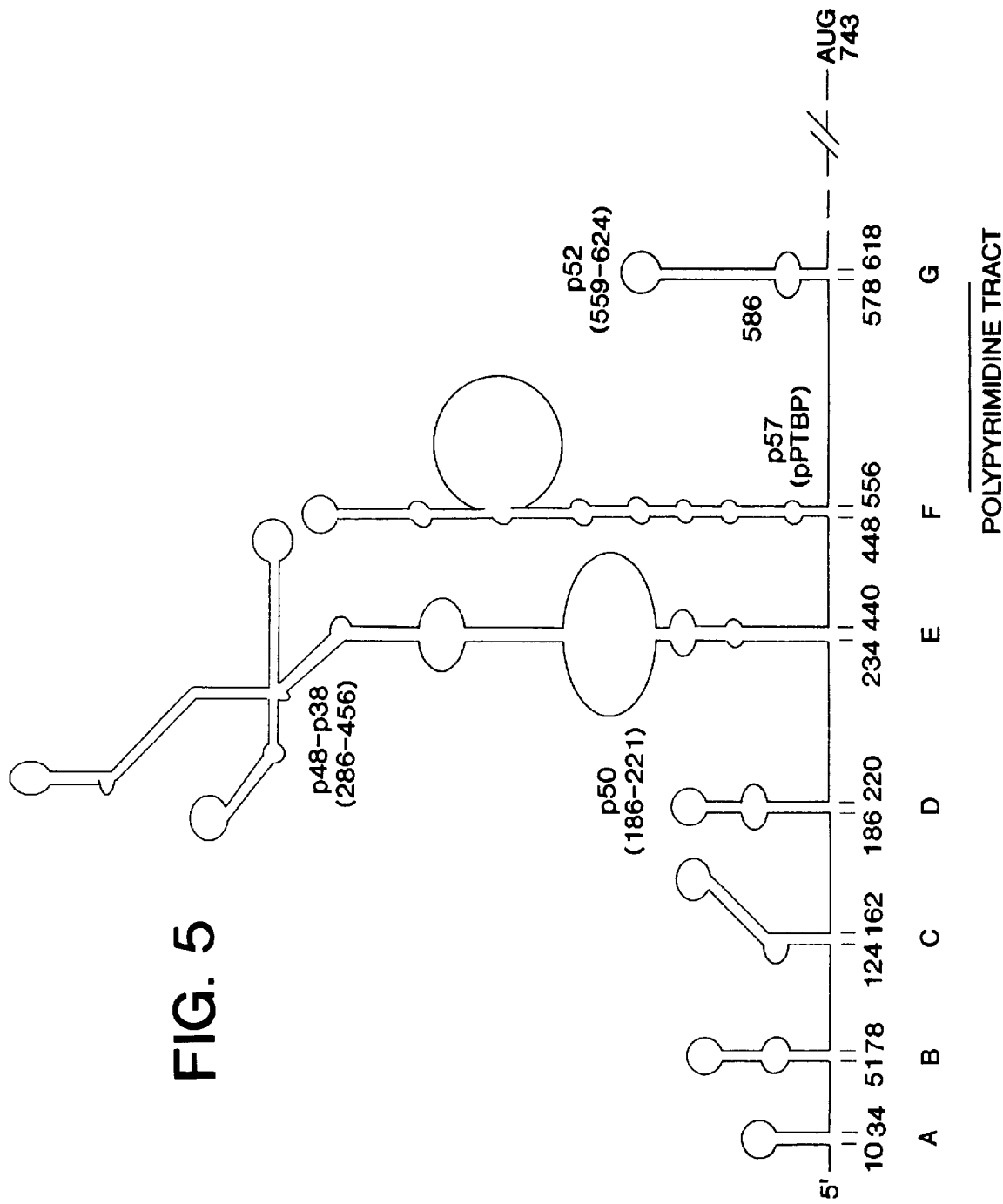
FIG. 5 illustrates the predicted secondary structure of the 5'UTR of poliovirus RNA showing possible interaction sites with cellular proteins by different structural domains. The molecular masses of the cellular proteins with their possible sites of interactions (indicated by the nucleotides within parentheses) are shown. The figure is a modified version of secondary structure predictions published by Pilipenko et al. (1992, supra), Jackson et al. (1990, supra) and Dildine, S. L. et al. *J Virology* (1992) 66:4364–4376.

Demonstration that the Yeast Inhibitor RNA Competes with Both Stem-loops D and G for Protein Binding Poliovirus 5'UTR contains several thermodynamically stable stem-loop structures that are believed to play important roles in viral RNA replication and translation (FIG. 5). Among these, stem-loops A, B and C are presumably involved in RNA replication. On the other hand stem-loops D-G are believed to be involved in viral mRNA translation (Dildine et al. 1992). Stem-loop D (SL-D), comprising nucleotides 186–221, has been shown to bind a 50 kDa protein (p50) (Najita et al. (1990, supra)), whereas stem-loop G (SL-G), representing poliovirus 5'UTR sequences from 559–624, binds to a 52 kDa protein (p52) which has recently been identified as the human La protein (Meerovitch et al. (1993, supra)).

Figure 6A:
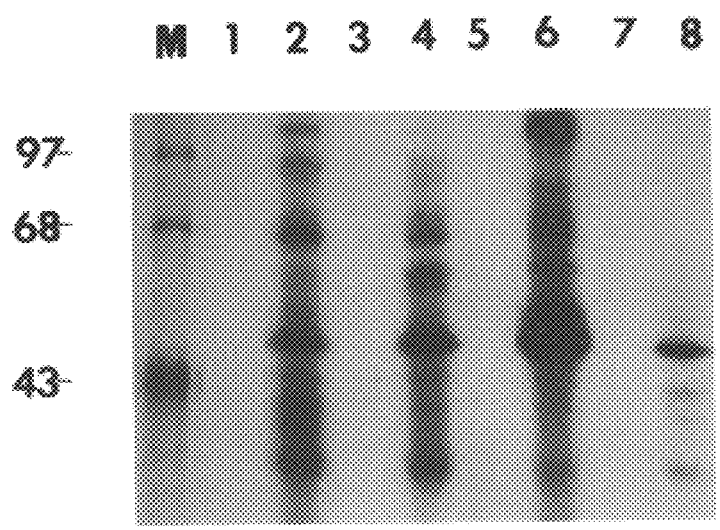
FIGS. 6A–6B illustrate UV crosslinking of HeLa cell proteins to $^{32}$P-labeled I-RNA, 5'UTR RNA, stem-loop SL-G and SL-D RNA probes.

Results presented in the previous Example indicated that the inhibitor RNA interacts with p52 which normally binds to stem-loop G within the viral 5'UTR. To determine if the inhibitor RNA is also capable of binding to p50 and competing with stem-loop D, an RNA corresponding to nucleotides 178–224 of the 5'UTR was prepared. In the first experiment individually $^{32}$P-labeled I-RNA, the whole 5'UTR, stem-loop G (UTR 559–624), and stem-loop D (UTR 178–224) were incubated separately with HeLa S-10 extract, and the resulting protein-nucleotide complexes were analyzed by UV-crosslinking as shown in FIG. 6A. A major protein-nucleotidyl complex of approximately 52 kDa was detected in all four reactions (lanes 2, 4, 6, and 8).

Figure 6B:
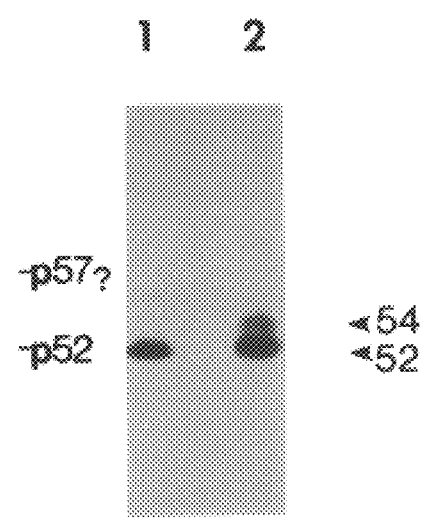

When stem-loop G was used as the labeled probe, an additional band at 54 kDa was detected (FIG. 6A, lane 6). Other crosslinked proteins ranging from 37 to 48 kDa were also detected with all four labeled probes. Because the lane showing protein binding by labeled stem-loop G (FIG. 6A, lane 6) was relatively overexposed, another experiment comparing binding of SL-G and SL-D was performed (FIG. 6B, lanes 1 and 2). This clearly shows that both stem-loops D and G bind proteins which migrate identically on the SDS-gel (52 kDa band).

To confirm the result that similar proteins may be interacting with I-RNA and stem-loops D and G, the following competition experiments were performed. $^{32}$P-labeled 5'UTR or SL-D (UTR 178–224) or SL-G (UTR 559–624) RNAs were incubated with HeLa S10 extract either alone or in the presence of unlabeled competing RNAs (e.g., 5'UTR, SL-D, I-RNA, SL-B, SL-C, nonspecific RNA). The resulting complexes were then analyzed by UV-crosslinking studies. RNA sequences representing stem-loops B and C (SL-B and SL-C) were used as negative controls.

Figure 7A:
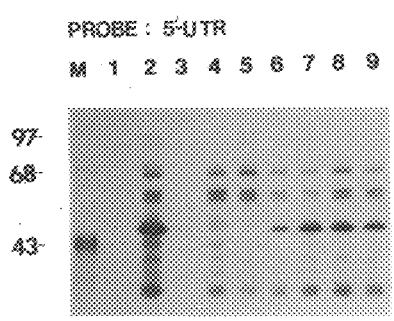
FIGS. 7A–7C show that I-RNA competes with both stem-loops SL-G and SL-D for protein binding. The $^{32}$P-labeled RNA probes used in the UV-crosslinking experiments are listed on top of each panel. The numbers at left of FIG. 7A indicate the molecular masses of protein markers in lane M.

When poliovirus 5'UTR was used as the labeled probe, almost complete inhibition of formation of the 52 kDa protein-nucleotidyl complex was observed with unlabeled UTR, I-RNA and stem-loop G (FIG. 7A, lanes 2–5). Stem-loop D partially competed with labeled 5'UTR for p52 binding (FIG. 7A, lane 6). Unlabeled SL-B, SL-C and a nonspecific RNA were relatively ineffective in competing with 5'UTR for p52 binding (FIG. 7A, lanes 7–9). Only unlabeled UTR RNA competed with the formation of all labeled bands whereas I-RNA and stem-loops G and D specifically inhibited formation of the p52 band.

Figure 7B:
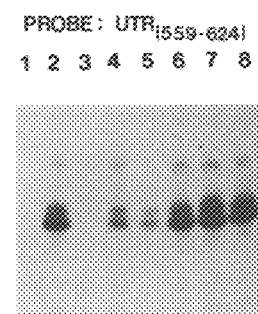
Figure 7C:
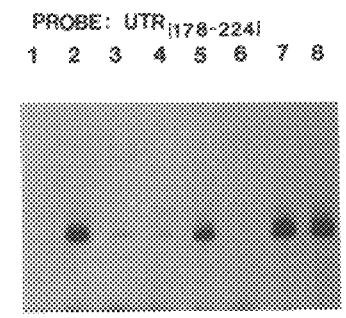

When stem-loop G was used as the labeled probe, a doublet migrating at 52 and 54 kDa was detected as expected (FIG. 7B, lane 2). Homologous competition with unlabeled SL-G completely inhibited formation of these complexes (FIG. 7B, lane 3). Almost 80% inhibition of formation of these UV-crosslinked complexes was observed in the presence of unlabeled I-RNA and SL-D RNA (lanes 4, 5). However, no inhibition was observed when an unrelated RNA and SL-B or SL-C RNAs were used as competitors (lanes 6–8). A similar result was obtained when radiolabeled SL-D RNA was used as the probe in the UV-crosslinking assay. Almost total inhibition of the formation of protein-nucleotidyl complex was observed in the presence of unlabeled I-RNA, SL-G RNA and the homologous SL-D RNA (FIG. 7C, lanes 2–4 and 6). As expected SL-B and SL-C RNAs were unable to successfully compete with the labeled SL-D probe.

Taken together these results show that a similar or identical protein having an approximate molecular weight of 52 kDa interacts with all three RNAs: stem-loops D and G, and I-RNA.

EXAMPLE 7

Demonstration that the Yeast Inhibitor RNA Preferentially Inhibits Internal Initiation of Translation In Vitro To examine whether the cloned and purified I-RNA preferentially inhibits internal initiation of translation from an RNA also initiated from a 5' cap, its effect on translation from a bicistronic messenger was determined. For this purpose, a bicistronic construct containing CAT and luciferase (LUC) genes flanked by the Thieler's Murine encephalomyelitis virus (TMEV) 5'UTR was obtained. TMEV 5'UTR is known to contain IRES sequences and has been shown to initiate translation internally (Bandopadhyay et al. 1992). Initiation of translation occurring internally from the TMEV 5'UTR would result in synthesis of luciferase, whereas cap-dependent translation would normally produce the CAT protein.

Figure 8A:
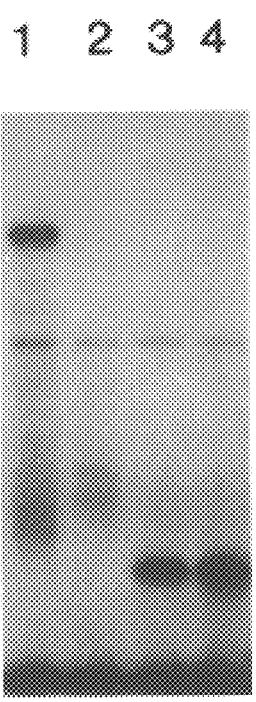
FIGS. 8A–8B demonstrate that I-RNA inhibits internal initiation of translation in vitro.
Figure 8B:
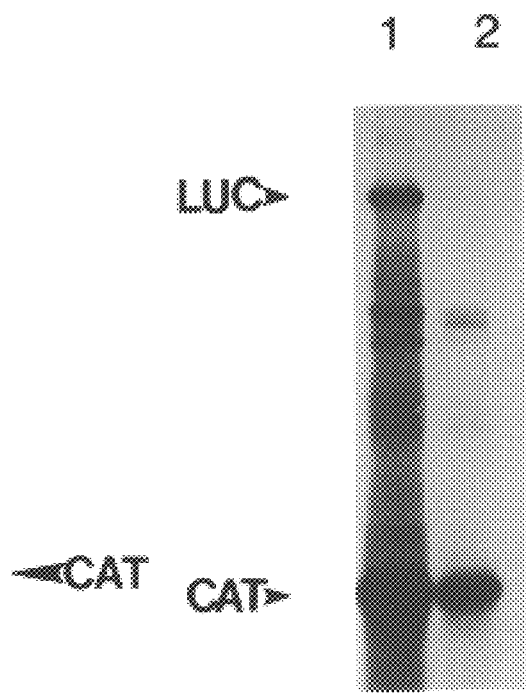

When translated in reticulocyte lysate, translation from the bicistronic message produced both CAT and luciferase proteins (FIG. 8B, lane 1). In the presence of the purified yeast inhibitor RNA, significant CAT synthesis was observed whereas synthesis of luciferase was almost completely inhibited. Quantitation of the labeled CAT and luciferase bands showed that luciferase synthesis was inhibited over 90% compared to the control, while only 20% inhibition of CAT synthesis was observed. Background incorporation in the translation reaction also was significantly less in the reaction containing the inhibitor, for reasons not completely understood.

Figure 11A:
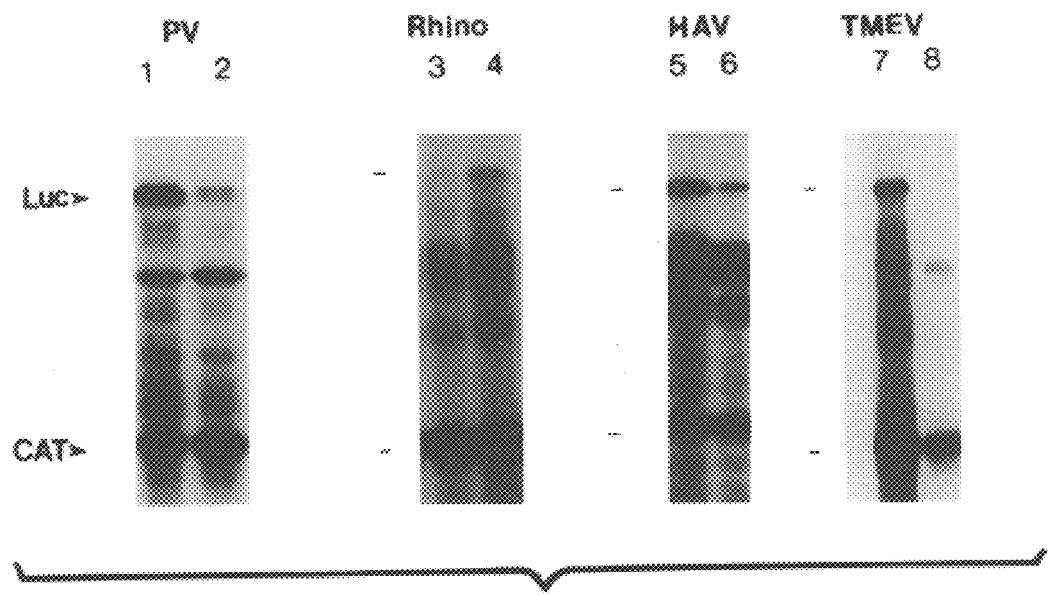
FIGS. 11A–11B show that yeast I-RNA specifically inhibits internal ribosome entry site (IRES)-mediated translation in vitro.
Figure 11B:
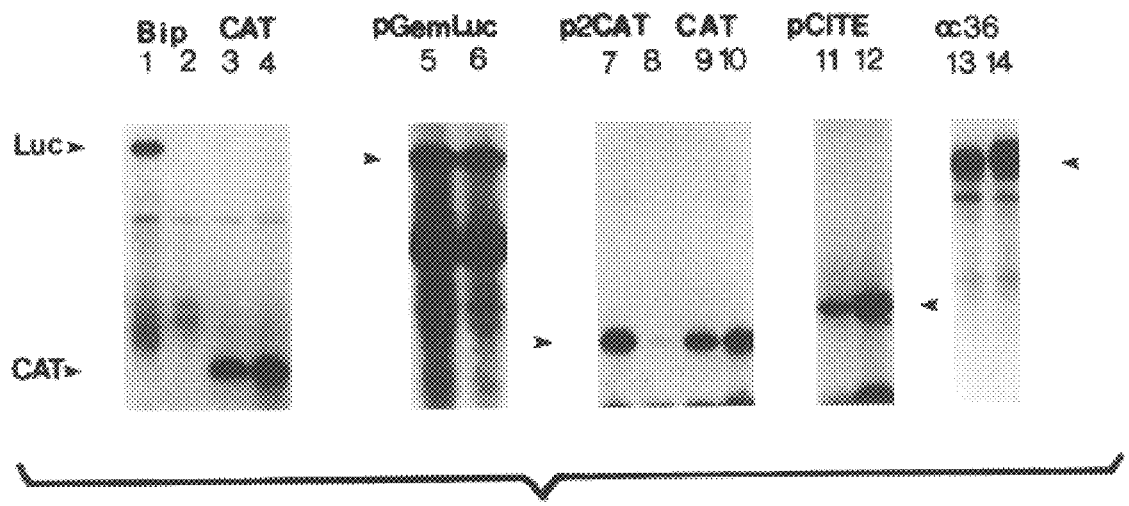

Using bicistronic RNA constructs it has been demonstrated that I-RNA preferentially inhibits internal ribosome entry site (IRES) mediated translation by a variety of picornaviral RNAs including those of poliovirus, rhinovirus, hepatitis A virus, TMEV virus, and the like. See, for instance, FIG. 11.

These results indicate that the yeast inhibitor RNA preferentially inhibits internal initiation of translation in a second viral control region, the TMEV 5'UTR.

EXAMPLE 8

Demonstration that the Yeast Inhibitor RNA Inhibits Internal Initiation of a Cellular mRNA Recent results have shown that some cellular mRNAs initiate translation internally (Macejak et al. 1991; Oh et al. 1992). For instance, the immunoglobulin heavy chain binding protein (Bip) can be synthesized by internal initiation. To determine whether Bip synthesis can be specifically inhibited by the inhibitor RNA, a construct containing the 5'UTR of Bip mRNA linked to a reporter gene (luciferase) was obtained from P. Sarnow (Univ. of Colorado). Translation of this mRNA in HeLa extracts generated the luciferase protein (FIG. 8A, lane 1). Addition of the yeast inhibitor RNA completely inhibited luciferase synthesis from this RNA construct (lane 2). As expected, cap-dependent translation from a CAT construct was not at all inhibited under the same conditions (lanes 3 and 4). In fact, CAT translation was significantly stimulated over the control as previously observed (Coward et al. 1992, supra). These results indicate that the yeast inhibitor RNA was capable of inhibiting internal initiation from a cellular mRNA as well as a viral mRNA.

EXAMPLE 9

Demonstration of Inhibition of Translation of Poliovirus RNA in vivo

To determine whether the cloned inhibitor RNA inhibits translation of poliovirus RNA in vivo, poliovirus RNA was transfected into HeLa cells alone or together with the purified yeast RNA. HeLa cell monolayers were grown in tissue culture flask in minimal essential medium (GIBCO) supplemented with 5% fetal bovine serum. Poliovirus RNA (type 1 Mahoney) was isolated from infected HeLa cells as described earlier (Dasgupta, 1983). Synthetic I-RNA or polio RNA were mixed with carrier yeast tRNA to yield a total 20 $\mu$g RNA per transfection reaction. The RNA samples were then mixed with 30 $\mu$g of Lipofectin (GIBCO-REL) and 20 units of RNasin (Promega) and incubated for 30 min at room temperature. Finally, the samples were mixed with 4 ml of minimal essential medium (GIBCO) containing 2.5% fetal bovine serum, and added to petri dishes containing 70–80% confluent HeLa monolayer cells. The cells were then incubated at 37° C. in a $CO_2$ incubator for 24 hr.

Figure 9:
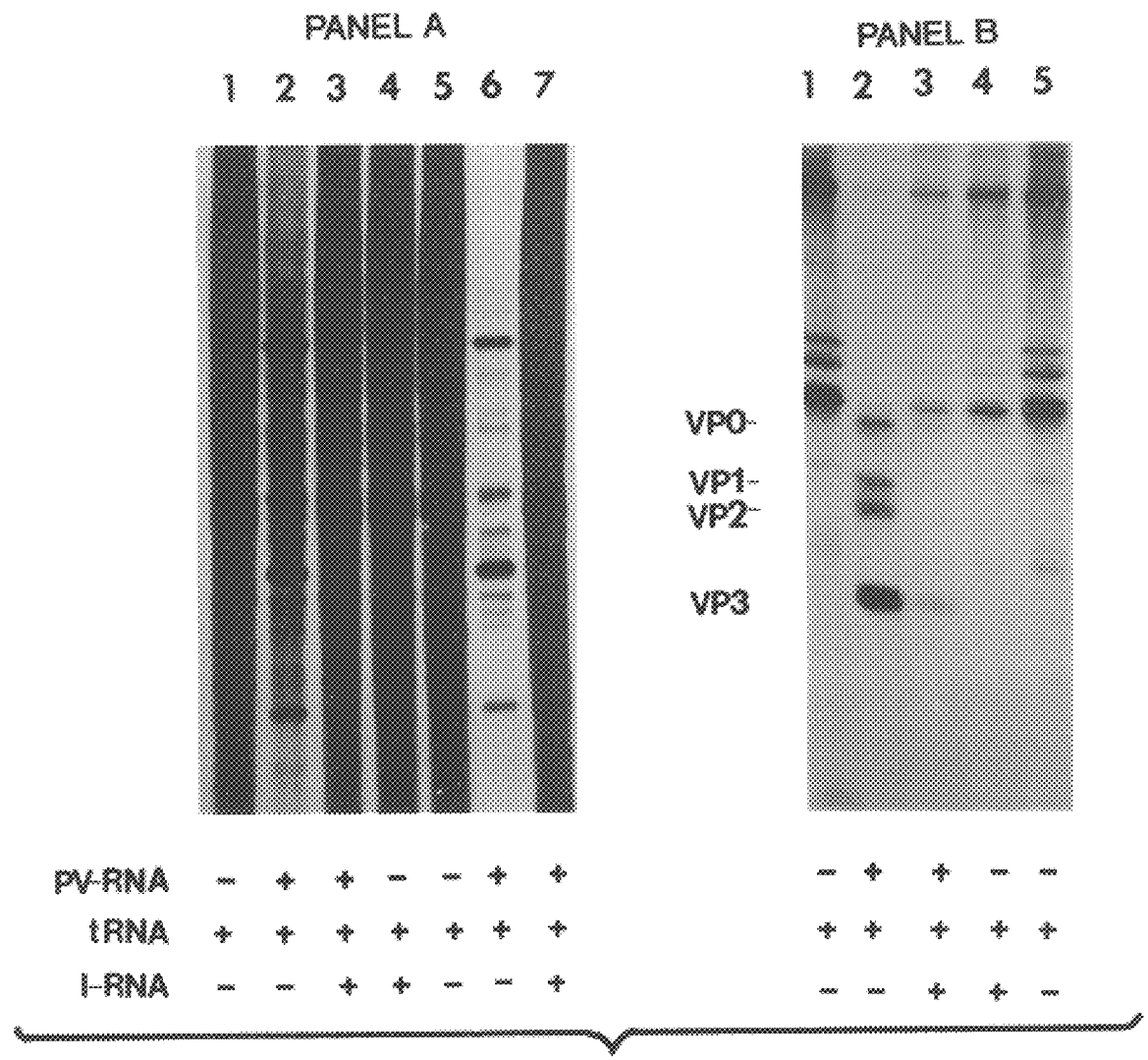
FIG. 9 shows that I-RNA inhibits translation of poliovirus RNA in vivo. Monolayers of HeLa cells were transfected with viral RNA alone, I-RNA alone or viral RNA and I-RNA together. After transfection the cells were labeled with $^{35}$S-methionine and in vivo labeled proteins were analyzed on a SDS-14% polyacrylamide gel either directly (panel A) or after immunoprecipitation with anticapsid antibody (panel B) as described in the examples below. Panel A: The RNAs added to each transfection reaction are as indicated in the figure. Panel B: The panel shows the immunoprecipitated in vivo labeled proteins from the transfection reactions shown in panel A, lanes 1–5. The positions of the poliovirus capsid proteins are indicated to the left of panel B.

Proteins were labeled by addition of $^{35}$S-methionine and synthesis of viral proteins was monitored by direct analysis of cell-free extracts (FIG. 9, panel A) or by immunoprecipitation of viral capsid proteins by anticapsid antisera (FIG. 9, panel B). More in particular, for in vivo labeling of proteins after transfection, cells were preincubated in methionine-free medium (MEM, GIBCO) for 40 min at 37° C. Then 100 $\mu$Ci of the trans labeled methionine (sp. act.>1000 Ci/mmole) was added to the cells and incubation was continued for another hour. 35S-methionine-labeled HeLa cell extract was prepared as described previously (Ransone et al. 1987).

In vivo labeled viral proteins in transfected cells were detected by immunoprecipitation with poliovirus anticapsid antibody (purchased from American Type Culture Collection). Immunoprecipitations were performed overnight at 40° C. with 5 $\mu$l of anticapsid antibody in a 500 $\mu$l reaction volume containing IxRIPA buffer (5 mM Tris pH 7.9, 150 mM NaCl, 1% Triton X100, 0.1% SDS, 1% Sodium deoxycholate). The immune complexes were precipitated with protein A Sepharose (75 $\mu$l of a 20% solution in RIPA buffer plus 0.2% BSA) and then analyzed on a SDS-14% polyacrylamide gel as described earlier (Coward et al. 1992, supra).

In the absence of added viral RNA and the inhibitor RNA, synthesis of cellular proteins was evident (panel A, lane 1). When viral RNA (1 $\mu$g) was transfected into cells, synthesis of distinct viral proteins was observed (lane 2). In addition, the background of host cell proteins diminished considerably due to shut-off of host cell protein synthesis by poliovirus (lane 2).

When the inhibitor RNA was cotransfected with viral RNA (1 $\mu$g) into HeLa cells, no detectable synthesis of viral proteins was observed and host cell protein synthesis was restored (lane 3). Expression of the inhibitor RNA alone did not interfere with the synthesis of cellular proteins (lane 4). Lane 5 (panel A) shows that carrier tRNA used in transfection experiments had no effect on cellular protein synthesis.

Transfection of cells with an increased amount of poliovirus RNA (2 $\mu$g) resulted in synthesis of viral proteins and a more pronounced shut-off of cellular protein synthesis (lane 6). However, in the presence of the inhibitor RNA, viral protein synthesis was inhibited and host cell protein synthesis was restored (lane 7) to the level seen in the control reaction. The results shown in panel B confirmed the fact that viral protein synthesis was inhibited in cells containing the inhibitor RNA. Synthesis of viral capsid proteins was inhibited in cells cotransfected with viral RNA and the inhibitor RNA (lane 3, panel B).

Therefore, the yeast inhibitor RNA efficiently inhibited translation of poliovirus RNA in vivo. Further, protection of monolayer cells from the cytolytic effects of poliovirus infection in the presence of the yeast inhibitor RNA paralleled restoration of host cell protein synthesis seen in lanes 3 and 7 (FIG. 9A).

EXAMPLE 10

Analysis of Deletion Mutants of Yeast I-RNA

Figure 16:
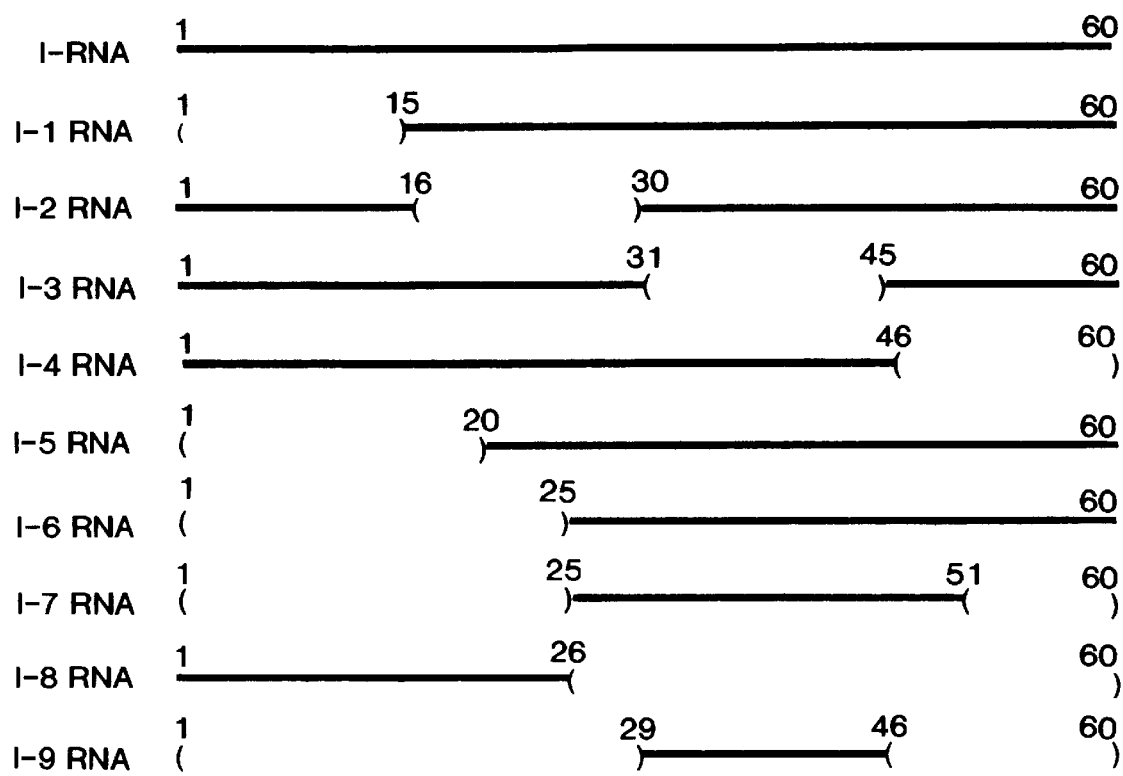
FIG. 16 diagrams I-RNA deletion mutant constructs tested for translation inhibiting activity. The nucleotide positions of the mutation sites are indicated for each mutant. The names of the respective mutants are listed at the far left.

To determine I-RNA sequences required for inhibition of poliovirus IRES-mediated translation, a nested set of 15 nt long deletions of the yeast I-RNA sequence was generated (designated I-1, I-2, I-3, and I-4; FIG. 16). I-RNA deletion mutants were generated by in vitro transcription with T7 RNA polymerase from oligonucleotide templates. Different lengths of oligonucleotides were synthesized (Biosynthesis Inc.) each beginning with a T7 promoter adapter sequences followed by various lengths from different regions of I-RNA sequences. ligodeoxyribonucleotide templates were mixed with equimolar amounts of the 17 mer T7 primer oligonucleotide in 0.1M NaCl, and annealed by heating at 100° C. for 5 min followed by slow cooling to room temperature. The nucleotide positions of the different I-RNA deletion mutants are shown in FIG. 16.

Effects of truncated I-RNA mutants on in vitro translation programmed by P2 CAT RNA containing the poliovirus 5 UTR were determined. Both I-1 and I-2 RNAs were still active in translation-inhibition, although they were not as active as intact I-RNA. Deletion of nucleotides 31–45 or 46–60 (I-3 or I-4) from the I-RNA, however, almost totally destroyed the ability to inhibit IRES-mediated translation, as shown by inhibition of in vitro translation in HeLa lysates programmed by the 5'-UTR of poliovirus RNA. In particular, the effects of different I-RNA deletion mutants on in vitro translation of pG3CAT and P2CAT RNAs in HeLa lysates were determined. in vitro translations were performed with approximately 2 pg of either uncapped p2CAT RNA or capped pG3CAT RNA in the absence or presence of the 2 pg of deleted I-RNAs.

Figure 3:
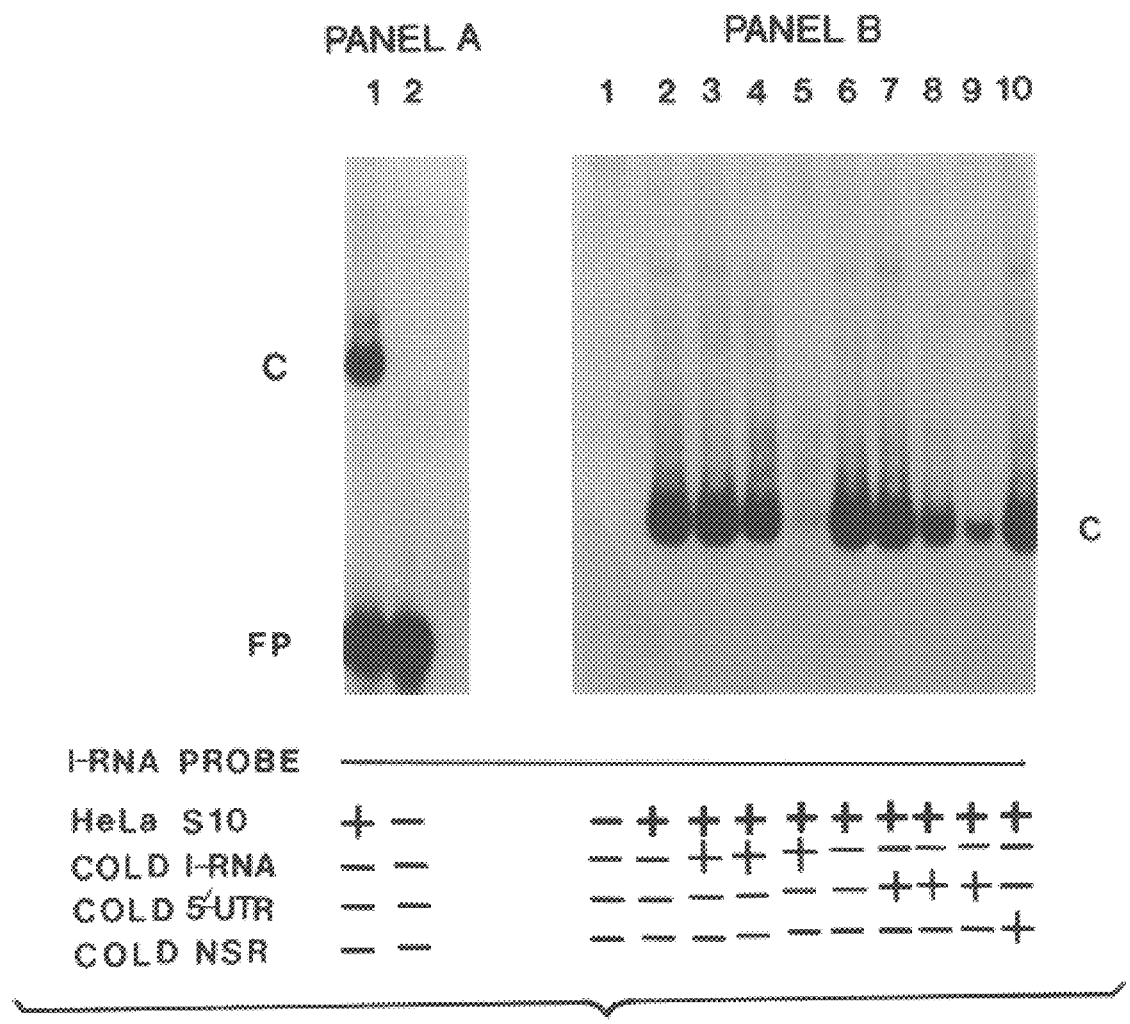
FIG. 3 illustrates formation of a complex between the I-RNA and cellular proteins which retards the I-RNA during gel electrophoresis and is competitively inhibited by the 5'-UTR of the poliovirus RNA. $^{32}$P-labeled I-RNA probe was incubated with or without HeLa S-10 extract in the binding reactions as described in the examples below. The RNA-protein complexes were analyzed on a nondenaturing 4% polyacrylamide gel. Panel A shows the mobility shift from free probe (FP) in absence of the S-10 extract (lane 2) to the complexed form (C) in presence of the S-10 extract. Panel B shows the results of the competition experiments with unlabeled competitor RNAs. Ten, 50 and 100-fold molar excesses of unlabeled I-RNA (lanes 3–5) or unlabeled 5'-UTR (lanes 7–9) were used in the binding reactions. The reaction in lane 10 contained loo-fold molar excess of unlabeled nonspecific RNA (NSP).

The results of these tests indicated that the 3'-terminal half of the I-RNA contains major sequences necessary for inhibition of viral IRES-mediated translation. However, sequences present within the first 15 nucleotides (i.e., deleted in I-1) or the next 15 nucleotides (I-2) also play a role in inhibition, since mutants lacking these sequences are not as active as intact I-RNA. Further deletion analysis showed that a 25 nt long fragment of I-RNA (1–7 RNA, nt 26–50) was as active as I-RNA in viral translation-inhibition. A similar deletion mutant that contained an extra 10 nucleotides at its 3'-end (I-6 RNA, nt 26–60) also was active, but not as active as I-7 RNA. A fragment of I-RNA containing nt 1–25 (I-8 RNA), however, was totally inactive in translation inhibition. Further deletion of I-7 RNA resulted in a smaller fragment (I-9, nt 30–45) which was capable of inhibiting IRES-mediated translation. The ability of this fragment (I-9) to inhibit translation is fully consistent with the previously noted inability of I-3 RNA to arrest translation since I-3 RNA lacks nts 31–45 (FIG. 3).

None of the tested mutant I-RNAs was able to inhibit cap-dependent translation of pCAT RNA.

To determine whether the truncated I-RNAs are capable of inhibiting internal initiation of translation, their effects on translation from a bicistronic construct were determined. A bicistronic construct containing CAT and luciferase (LUC) genes flanked by the poliovirus 5'UTR was used in this experiment. Initiation of cap-independent translation occurring internally from the poliovirus 5'UTR would result in the synthesis of luciferase, whereas cap-dependent translation would normally produce the CAT protein. In uninfected HeLa cell extract, translation from the capped bicistronic message produced both CAT and luciferase proteins in separate experiments using different cell extracts. Addition of full length I-RNA preferentially inhibited synthesis of luciferase but not that of CAT. The 25 nt long I-7 RNA almost totally inhibited production of luciferase. CAT synthesis, however, was significantly stimulated in reactions containing I-7 RNA.

No inhibition of luciferase synthesis was apparent with the mutant I-4 RNA. Synthesis of CAT protein was also stimulated by I-4 RNA. Similar results were obtained with I-9 and I-8 RNAs. The 16 nt long I-9 RNA inhibited luciferase synthesis significantly compared to the control. Although 20% inhibition of CAT production was observed in presence of I-9 RNA, luciferase synthesis was inhibited almost 85% over the control. In contrast, I-8 RNA did not significantly inhibit synthesis of either luciferase or CAT. These results suggest that I-7 and I-9 RNAs, but not I-4 and I-8 RNAs, preferentially inhibit internal initiation of translation programmed by poliovirus 5 UTR.

To determine whether mutant I-RNAs inhibit translation of poliovirus RNA in vivo, poliovirus RNA was transfected (using liposomes) into HeLa cells singly or together with purified I-7, I-9, I-4, I-8 and I-RNA. Proteins were labeled by $^{35}$S-methionine and the synthesis of viral proteins was monitored by immunoprecipitation of viral capsid proteins from cell extracts by anti-capsid antisera. No capsid protein could be precipitated from mock-transfected cells. Upon transfection of cells with poliovirus RNA alone, synthesis of capsid proteins was clearly detected. Cotransfection of I-7 RNA or I-RNA with poliovirus RNA resulted in over 90% inhibition of capsid protein synthesis. Activity of I-9 RNA was approximately 50% of that observed with 1–7 or I-RNA. Higher concentrations of I-9 RNA, however, inhibited viral protein synthesis to the extent seen with I-7 RNA. As expected, I-8 RNA and I-4 RNA were unable to inhibit translation of viral proteins. It should be noted that similar amounts of intracellular poliovirus RNAs were detected in both cells transfected with poliovirus RNA alone and those transfected with a mixture of PV RNA and I-7 or I-9 RNAs, suggesting that the stability of PV RNA is not altered significantly in cells containing I-RNA or its derivatives.

EXAMPLE 11

Identification of Cellular Proteins that Interact with Full Length and Deleted I-RNAs The 52 kDa I-RNA binding protein described above was shown to be identical to the human La autoantigen and various other cellular protein factors were shown to bind to full-length or deleted I-RNAs.

For mobility shift experiments, fifty micrograms of HeLa S10 extract or 10 pg of HeLa ribosomal salt wash (RSW) was preincubated at 30° C. for 10 min with 4 pg of poly (dI-dC) (Pharmacia) in a 15 μl reaction mixture containing 5 mM HEPES (pH 7.6), 25 mM KCl, 2 mM MgCl2, 2 mM-DTT, 0.1 mM EDTA, 1.5 mM ATP, 2 mM GTP, and 3.8% glycerol. For competition experiments 100 fold molar excesses of unlabelled competitor RNAs were added to the reaction and incubated for 10 min at 30° C. Finally, 5 to 10 fmol of labeled RNA probe was added to respective reaction mixtures and the incubation continued for another 20 min at 30° C. Three microliters of gel loading dye was added to the reaction mixture to a final concentration of 5% glycerol and 0.02% each of bromophenol blue and xylene cyanol. For supershift assay the S10 extract was preincubated with either 2.5 μl of either nonimmune human sera or 2.5 μl of immune human sera against La protein on ice for 10 min, the respective 32P-labeled RNA probe was then added to the reaction mixture and incubation was continued for another 20 min on ice. The RNA protein complexes were then analyzed on a 4% polyacrylamide gel (39:1 ratio of acrylamide:bis) containing 5% glycerol in 0.5×TBE.

For UV-induced crosslinking and immunoprecipitation analyses, 32P-labeled RNA-protein complexes generated as described above were irradiated with a UV lamp (multi band UV) 254/366 nm (model UGL; 25 UVP Inc.) at a distance of 2 to 3 cm for 15 min in a microtiter plate. Unbound RNAs were then digested with a mixture of 20 μg RNase A and 20 units of RNase T1 at 37° C. for 15 min. For immunoprecipitation of labeled complexes, 2–5 Al of either nonimmune human sera or immune human sera from a patient with lupus disease (standard reference La antibody) were added and kept on ice for 2h in the presence of 200 μl×RIPA buffer [5 mM Tris(pH 7.9), 150 mM NaCl, 1% Triton-X 100, 0.1% SDS and 1% sodium deoxycholate). Five mg of protein A sepharose was then added to the respective reaction tubes, rocked in the cold room for 1h, then centrifuged at 12,000 rpm for 5 min at 4° C. Beads were washed with 1×RIPA three times to reduce nonspecific binding. Finally, resuspended beads in 1×SDS gel loading dye (50 mM Tris [pH 6.8], 100 mM DTT 2% SDS, 0.1% BPB, 10% glycerol) were heated at 100° C. for 5 min. and analyzed on a SDS 14% polyacrylamide gel.

As shown in FIG. 12, a gel-retarded complex (denoted C) containing labeled I-RNA and HeLa cell proteins was supershifted (denoted SC) by an antibody to the human La protein (FIG. 12, left gel, lanes 3 and 4). A similar complex formed with labeled I-RNA and purified recombinant La protein (lane 5, complex C) can also be supershifted with anti-La antibody to the same relative position as found with HeLa cell extract. A second slower migrating complex was also observed with purified La protein (lane 5), the majority of which could not be supershifted with anti-La antibody (lane 6). These results suggest that complex C formed by incubating labeled I-RNA and HeLa cell extract contains La autoantigen. To confirm that complex C indeed contains La protein, UV-crosslinking studies were performed with $^{32}$P-labeled I-RNA or 5'-UTR (559–624 nt) probes using HeLa cell extract or purified La protein. UV-crosslinked complexes were then immunoprecipitated with anti-La or nonimmune sera and analyzed by SDS-PAGE. A 52 kDa UV-crosslinked protein was specifically immunoprecipitated by anti-La antibody when complexes were formed with HeLa cell extract using either labeled I-RNA or UTR probes (FIG. 12, right gel, lanes 2 and 5). This 52 kDa band co-migrated with UV-crosslinked, anti-La immunoprecipitated complex formed by incubating purified La protein with $^{32}$p I-RNA (lane 3) or $^{32}$p 5'-UTR (lane 6). A prominent ~120 kDa complex seen in lanes 2 and 5 was not specific to La antibody as it could also be detected in lanes containing nonimmune serum. These results demonstrate that I-RNA interacts with the human La autoantigen.

The identity of the p52 protein bound by I-RNA was further confirmed by demonstrating that inhibition of IRES-mediated translation by I-RNA is reversed by addition of La antigen. Poliovirus is known to inhibit cap-dependent translation of host cell mRNAs by proteolytically cleaving the p220 component of the cap-binding protein complex. Therefore, extracts derived from virus-infected cells are only active in cap-independent IRES-mediated translation but not cap-dependent translation.

To determine whether I-RNA-induced inhibition of IRES-mediated translation can be specifically rescued by addition of exogenous purified La protein, translation of p2CAT RNA (5-UTR-CAT) was performed in virus-infected cell extracts. Translation of p2 CAT RNA in PV-infected HeLa cell extract was inhibited significantly by I-RNA. Significant stimulation of viral 5'-UTR-mediated translation was observed when purified La protein was added to the infected cell extract. This is probably due to a limiting amount of La protein in virus-infected cells. Inhibition of translation mediated by I-RNA can be reversed by addition of purified La protein, almost to the extent seen in extract containing La protein alone. In contrast, addition of an equivalent amount of BSA failed to restore IRES-mediated translation. A similar result was observed when mock-infected extracts were used instead of virus-infected cell extracts.

Binding of various protein factors to 1-RNA mutants also was examined. Results presented above demonstrated differential activity of various I-RNA mutants in inhibiting IRES-mediated translation. While I-7 and I-9 RNAs were capable of inhibiting poliovirus IRES-mediated translation, I-4 and I-8 RNAs were almost totally inactive as translation inhibitors. To determine whether similar or different proteins were bound by these RNAs, various labeled RNA probes were incubated with HeLa proteins and protein-RNA complexes were examined by UV-crosslinking following ribonuclease digestion.

Two sources of HeLa proteins were used for these experiments, S10 and ribosomal salt wash (RSW). HeLa Cell free extract (S10) and RSW preparation. HeLa S10 cell extracts were prepared as described hereinabove. Ribosomal salt wash from HeLa cells was prepared as described by Brown and Ehrenfeld (33) with some modifications. Cultures of HeLa cells ($4\times10^5$ cells/ml) were harvested by centrifugation, washed three times with cold isotonic buffer (35 mM HEPES, pH 7.5, 146 mM NaCl, 11 mM glucose) and resuspended in two times packed cell volume of lysis buffer (10 mM KCl 1.5 mM Mg acetate, 20 mM HEPES, pH 7.4, and 1 mM DTT) followed by incubation on ice for 10 min for swelling. Cells were disrupted at O/C with 50 strokes in a type B dounce homogenizer. After disruption extracts were centrifuged for 15 min at 10,000 rpm at 4/C in Sorvall SS34 rotor to remove nuclei and mitochondrial fractions. The supernatant (S10 extract) was centrifuged at 50,000 rpm for 2h at 4/C in a Beckman Ti6O rotor. The ribosome pellet was resuspended at a concentration of approximately 250 A260/ml in lysis buffer with gentle shaking on an ice bath. KCl concentration was then adjusted to 500 mM and the solution was stirred for 30 min on an ice bath. The resulting solution was centrifuged for 2 h at 50,000 rpm at 4° C. The supernatant (salt wash) was then subjected to 0–70% ammonium sulfate precipitation. The pellet containing initiation factors was dissolved in low volume of dialysis buffer (without glycerol) followed by overnight dialysis at 4° C. against the dialysis buffer containing 5 mM Tris(pH 7.5), 100 mM KCl, 0.05 mM EDTA, 1 mM DTT and 5% glycerol. The dialysate was then centrifuged at 10,000 rpm for 10 min at 4° C. and the supernatant was aliquoted in small volumes into several prechilled tubes and stored at −70° C.

When full-length labeled I-RNA was incubated with HeLa S10 extract, two major bands having approximate molecular weights of 52 kDa and 110 kDa were detected in addition to minor bands at 100, 70, 48 and 46 kDa. When ribosomal salt wash proteins were used, the profile of protein-nucleotidyl complexes was significantly different from that with S10. First, the 110 kDa band was present in very low amounts in reactions containing RSW. Secondly, the 52 kDa protein was present as a doublet of 54–52 kDa and in relatively lower amounts compared to that in S10. Thirdly, new bands at approximately 80 and 37 kDa were apparent in RSW-containing reactions. In contrast to full-length I-RNA, when labeled truncated I-RNAs were used in UV-crosslinking experiments, the protein-nucleotidyl profile for each RNA was remarkably similar between S10 and RSW. While I-4 and I-8 RNAs bound mainly 70, 52, 48, 46 and 37 kDa polypeptides, I-7 and I-9 RNAs interacted with a new band at 80 kDa. The 80 kDa band was more pronounced with I-7 RNA. Additionally, the 70 kDa polypeptide bound by I-4 and I-8 RNAs was not detected with I-7 and I-9 RNAs. Another very high molecular weight polypeptide (running faster than the 220 kDa marker) was present only in reactions containing I-4 and I-8 RNAs. Similarly, in experiments utilizing RSW the 100 kDa polypeptide was preferentially bound by I-7 and I-9 RNAs. In competition experiments, it was observed that both unlabeled I-7 and I-4 RNAs successfully competed with all major protein bands bound by labeled I-7 and I-4 RNA probes. For example, all three polypeptides, 80 kDa, 52 kDa and 37 kDa, complexed to I-7 RNA were competed out with unlabeled I-7 RNA and I-4 RNA but not with a non-specific RNA. Similarly with labeled I-4 RNA, the 70, 52 and 37 kDa bands were competed with unlabeled I-7 and I-4 RNAs but not with a non-specific competitor. A higher molecular weight polypeptide was non-specifically bound to I-4 RNA as it could be totally competed out with a non-specific competitor. These results demonstrate that while the active I-7 and inactive I-4 RNAs bind the same two polypeptides (52 and 37 kDa), these two truncated I-RNAs differ from each other in binding at least one polypeptide: I-7 RNA binds the 80 kDa polypeptide, but I-4 RNA binds a 70 kDa polypeptide.

References Cited

Agol, V. I. *Adv virus Res* (1991) 40:103–180
Altman, M. et al. *Biochem Biophys Acta* (1990) 1050:155–159
Bandopadhyay, P. K. et al. *J Virol* (1992) 66:6249–6256
Belsham, G. J. et al. *J Virol* (1990) 64:5389–5395
Borman, A. et al. *Virology* (1992) 188:685–696
Borman, A. et al. *J Gen Virol* (1993) 74:1775–1788
Borovjagin, A. V. et al. *Nucleic Acids Res* (1991) 19:4999–5005
Brown, B. A. et al. *Virolooy* (1979) 97:376–405
Chang, K. H. et al. *J Virol* (1993) 67:6716–6725
Coward, P. et al. *J Virol* (1992) 66:286–295
Dasgupta, A. *Virology* (1983) 128:245–251
del Angel, Papvassiliou, A. G. *Proc Natl Acad Sci USA* (1989) 86:8299–8303
Dildine, S. L. et al. *J Virology* (1992) 66:4364–4376
Dorner, H. A. et al. *J Virol* (1984) 50:507–514
Gebhard, J. R. *J Virol* (1992) 66:3101–3109
Glass, M. J. et al. *Virology* (1993) 193:842–852
Haller, A. A. et al. *J Virol* (1992) 66:5075–5086
Hellen, C. U. T. et al. *Proc Natl Acad Sci USA* (1993) 90:7642–7646
Jackson, R. et al. *Trends Biochem Sci* (1990) 15:477–483
Jang, S. K. et al. *J Virol* (1988) 62:2636–2643
Jang, S. K. et al. *Enzyme* (1990) 44:292–309
Jang, S. K. et al. *Genes Dev* (1990) 4:1560–1572
Kitamura, N. et al. *Nature* London (1981) 291:547–553
Kohara, K. T. et al. *J Virol* (1992) 66:1476–1483
Kozak, M. *Microbiol Rev* (1983) 47:1–45
Luz, N. et al. *FEBS Letters* (1990) 269:311–314
Luz, N. et al. *Virology* (1991) 65:6486–6494
Macejak, D. G. et al. *Nature* London (1991) 353:90–94
Meerovitch, K. et al. *Genes Dev* (1989) 3:1026–1034
Meerovitch, K. et al. *J Virol* (1993) 67:3798–3807
Najita, L. et al. *Proc Natl Acad Sci USA* (1990) 87:5846–5850
Oh, S. K. et al. *Genes Dev* (1992) 6:1643–1653
Pearson, W. R. et al. *Proc Natl Acad Sci USA* (1988) 85:2444–2448
Pelletier, J. et al. *J Virol* (1988) 62:2219–2227
Pelletier, J. et al. *J Virol* (1988a) 62:4486–4492
Pelletier, J. et al. *Nature* London (1988) 334:320–325
Pelletier, J. et al. *Mol Cell Biol* (1988) 8:1103–1112
Pelletier, J. et al. *J Virol* (1989) 63:441–444
Percy, N. et al. *J Virol* (1992) 66:1695–1701
Pestova, T. V. et al. *J Virol* (1991) 65:6194–6204
Pilipenko, E. V. et al. *Cell* (1992) 68:119–131
Racaniello, V. R. et al. *Proc Natl Acad Sci USA* (1981) 78:4887–4891
Ransone, L. J. et al. *J Virol* (1987) 61:1781–1787
Rose, J. K. et al. *Proc Natl Acad Sci USA* (1978) 75:2732–2736
Rothblatt, J. A. et al. *Cell* (1986) 44:619–628
Skinner, M. A. et al. *J Mol Biol* (1989) 207:379–392

References cited by number

1. Tsukiyama-Korhara, K. l., N. Zuka, 51. Kohara, and A. Nomoto. 1992. Internal ribosome entry site within hepatitis C virus RNA. J. Virol, 66: 1476–1483.

2. Fukushi, S., K. Katayama, C. Kurillar.l, N. Islliyama, F. B. Hoshino, T. Andor and A. Oya. 1994. Complete 5'-non coding region is necessary for the efficient internal initiation of hepatitis C virus RNA. Biochem. Biophys. Res. Commun. 199:425–432.

3. Liu, D. X. M., and S. C. Inglis. 1992. Internal entry of Ribosomes on a tri-cistronic mRNA encoded by infectious bronchitis virus. J. Virol. 66:6143–6154.

4. Le, S. -Y., N. Sonenberg, and J. V. Maizel, Jr. 1994. Distinct structural elements and internal entry of ribosomes in mRNA3 encoded by Infectious Bronchitis Virus. Virology 198:405–411.

5. Chang, L. -J., P. Prycrak, and D. Ganem. 1989. Biosynthesis of the reverse transcriptase of hepatitis B viruses involves de novo translational initiation not ribosomal frame shifting. Nature 337:364–368.

6. Roy Choudury, S, C. Shih. 1990 Cis rescue of a mutated reverse transcriptase gene of human hepatitis B virus by creation of an internal ATG. J. Virol. 64:1063–1069.

7. Herman, R. C. 1986. Internal initiation of translation of the vesicular stomatitis virus phosphoprotein mRNA yields a second protein. J. Virol. 58:797–804.

8. Hassin, D., R. Korn, and M. S. Horwitz. 1986. A major internal initiation site for the in vitro translation of the adenovirus DNA polymerase. Virology. 155:214–224.

9. Curran, J., and D. Kolakofsky. 1989. Scanning independent ribosomal initiation of the Sendai virus Y proteins in vitro and in vivo. EMBO J. 8:521–526.

10. Das, S., P. Coward, and A. Dasgupta. 1994. A small yeast RNA selectively blocks internal initiation of translation programmed by poliovirus RNA: specific interaction with cellular proteins that bind to viral 5'-untranslated region. J. Virol. (In Press).

11. Pilipenko, E. V., Blinov, V. M., Romanova, L. I., Sinyakov, A. N., Maslova, S. V., and Agol, V. l. 1. 1989. Conserved structural domains in the 5'-untranslated region of picornaviral genomes: an analysis of the segment controlling translation and neurovirulence. Virology. 168:201–209.

12. Meerovitch, K., Y. V. Svitkin, I. S. Lee, F. Lejbkowicz, D. J. Kenan, E. K. L. Chan, V. l. Agol, J. D. Keene, and N. Sonenberg. 1993. La autoantigen enhances and corrects aberrant translation of poliovirus RNA in reticulocyte lysate. J. Virol. 67:3798–3807.

13. Svitkin, Y. V., K. Meerovitch, H. S. Lee, J. N. Phola Kia, D. Kenan, V. Agol, and N. Sonenberg. 1994. Internal translation initiation on poliovirus RNA: further characterization of La function in poliovirus translation in vitro. J. Virol. 68:1544–1550.

14. Das, S., and A. Dasgupta. 1993. Identification of the cleavage site and determinants required for poliovirus 3C-catalyzed cleavage of human TATA-binding transcription factor, TBP. J. Virol. 67:3326–3331.

15. Haller, A. A., J. H. C. Nguyen, and B. L. Semler. 1993. Minimum internal ribosome entry site required for poliovirus infectivity. J. Virol. 67:7461–7471.

16. Molla, A., A. V. Paul, and E. Wimmer. 1991. Cell-free, de novo synthesis of poliovirus. Science. 254: 1647–1651.

17. Barton, D. J., and J. B. Flanegan. 1993. Coupled translation and replication of poliovirus RNA in vitro: synthesis of functional 3D polymerase and infections virus. J. Virol. 67:822–831.

18. Kooter, J. M., and Borst, P. 1984. Alpha-amanitin insensitive transcription of variant surface glycoprotein genes provide further evidence for discontinuous transcription in trypanosomes. Nucl. Acid Res. 12: 9457–9472.

19. Dasgupta, A. 1983. Purification of host factor required for in vitro transcription of poliovirus RNA. Virology. 128:245–951.

20. Takeda, N., C. F. Yang, R. J. Kuhn, and E. Wimmer. 1987. Uridylylation of the genome-linked proteins of poliovirus in vitro is dependent upon an endogenous RNA template. Virus Res. 8: 193–204.

21. Toyoda, H., C. F. Yang, A. Nomoto, and E. Wimmer. 1987. Analysis of RNA synthesis of type I polio virus by using an in vitro molecular genetic approach. J. Virol. 61:2816–2822

22. Borman, A., M. T. Howell, J. G. Patton, and R. J. Jackson. 1993. The involvement of a splicesome component in internal initiation of human rhinovirus RNA translation. J. Gen. Virol. 74: 1775–1788.

23. Pattanaik, A., Ball, L. A., LeGrone, A. W., and Wertz, G. W. 1992. Infectious defective interfering particles of VSV from transcripts of a cDNA clone. Cell 69:1011–1020.

24. Sharmeen, L., Kuo, M. Y. P., Dinter-Gottlieb, G., and Taylor, J. 1988. Antigenomic RNA of human hepatitis delta virus can undergo self cleavage. J. Virol. 62:2674–2679.

25. Coward, P., and A. Dasgupta. (1992). Yeast cells are incapable of translating RNAs containing the poliovirus 5'-untranslated region: evidence for a translational inhibitor. J. Virol. 66:286–295.

26. Chambers, J. C., D. Kenan, B. J. Martin, and J. D. Keene. 1988. Genomic structure and amino acid sequence s of the human La auto antigen. J. Biol. Chem 263:18043–18051.

27. Meerovitch, K., J. Pelletier, and N. Sonenberg. 1989. A cellular protein that binds to the 5'-noncoding region of poliovirus RNA: implications for internal translation initiation. Genes Dev. 3:1026–1034.

28. Hellen, C. U. T., T. V. Pestova, M. Litterst, and E. Wimmer. 1994. The cellular polypeptide p57 (pyrimidine tract-binding protein) binds to multiple sites in the poliovirus 5'nontranslated region. Virology. 68:941–950.

29. Berlioz, C., and J. L. Darlix (1995). An internal ribosomal entry mechanism promotes translation of Murine Leukemia Virus gag polyprotein precursors. J. Virol. 69:2214–2222.

30. Poole, T. L., R. A. Popp, L. N. Potgieter, A. Siddique, M. S. Collett. (1995). Pestivirus translation initiation occurs by internal ribosome entry. Virology 206:750–754.

31. Riechman, J. L., S. Lain, J. A. Garcia. (1991). Identification of the initiation codon of plum pox potyvirus genomic RNA. Virology 185:544–552.

32. He, W. W., J. K. Lindzey, J. L. Prescott, M. V. Kumar, D. J. Tindall. (1994). The androgen receptor in the testicular feminized (Tfm) mouse may be a product of internal translation initiation. Receptor (1994, Summer) 4(2):121–134.

33. Brown, B. A., and E. Ehrenfeld (1979). Translation of poliovirus RNA in vitro: changes in cleavage pattern and initiation sites by ribosomal salt wash. Virology 97:396–405.

By application of the principles described and exemplified above, it is apparent that one of ordinary skill in the art could design an effective inhibitor RNA or structural mimic thereof and determine optimum conditions of translation inhibition according to the present invention, for any desired target RNA on which translation is initiated at an internal ribosome binding site by binding of one or more protein factors.

The entire disclosure of each publication cited herein is hereby incorporated herein by reference.

We claim:

1. A molecule that inhibits translation of an mRNA, which translation is initiated at an internal ribosome entry site of said mRNA and requires binding of a protein factor to said site, said molecule selectively binding to said factor, thereby preventing said factor from binding to said site of said mRNA, wherein said molecule is an RNA oligonucleotide consisting of less than 35 nucleotides, and wherein the nucleotide sequence of said RNA oligonucleotide is 5'GCGCGGGCAGCGCA3'(SEQ ID NO:1).

2. An isolated nucleic acid molecule selected from the group consisting of:

a nucleic acid molecule with the nucleotide sequence GCGCGGGCAGCGA (SEQ. ID NO1);

a nucleic acid molecule with the nucleotide sequence depicted in SEQ. ID NO:2; and a nucleic acid molecule comprising 15 or more contiguous nucleotides of SEQ. ID NO:2.

3. The nucleic acid molecule of claim 2, wherein said nucleic acid molecule is an RNA molecule.

4. An expression construct comprising DNA encoding the RNA molecule of claim 3 operably linked to an expression control sequence.

* * * * *